US010932724B2

(12) United States Patent
Addison et al.

(10) Patent No.: US 10,932,724 B2
(45) Date of Patent: Mar. 2, 2021

(54) SYSTEMS AND METHODS FOR MONITORING AUTOREGULATION USING A CONFIDENCE LEVEL

(71) Applicant: COVIDIEN LP, Mansfield, MA (US)

(72) Inventors: Paul S. Addison, Edinburgh (GB); Dean Montgomery, Edinburgh (GB); James N. Watson, Edinburgh (GB)

(73) Assignee: Covidien LP, Mansfield, MA (US)

( * ) Notice: Subject to any disclaimer, the term of this patent is extended or adjusted under 35 U.S.C. 154(b) by 519 days.

(21) Appl. No.: 15/184,305

(22) Filed: Jun. 16, 2016

(65) Prior Publication Data

US 2016/0367197 A1 Dec. 22, 2016

Related U.S. Application Data

(60) Provisional application No. 62/181,067, filed on Jun. 17, 2015.

(51) Int. Cl.
*A61B 5/02* (2006.01)
*A61B 5/00* (2006.01)
(Continued)

(52) U.S. Cl.
CPC .......... *A61B 5/7246* (2013.01); *A61B 5/0205* (2013.01); *A61B 5/02028* (2013.01);
(Continued)

(58) Field of Classification Search
CPC .............. A61B 5/7246; A61B 5/14551; A61B 5/02028; A61B 5/0205; A61B 5/14546; A61B 5/021
See application file for complete search history.

(56) References Cited

U.S. PATENT DOCUMENTS 4,776,339 A 10/1988 Schreiber
5,351,685 A 10/1994 Potratz
(Continued)

FOREIGN PATENT DOCUMENTS

EP 615723 A1 9/1994
WO WO9843071 A1 10/1998
(Continued)

OTHER PUBLICATIONS

Larson, Abby C., et al. "Cerebrovascular autoregulation after rewarming from hypothermia in a neonatal swine model of asphyxic brain injury." Journal of Applied Physiology 115.10 (2013): 1433-1442 (Year: 2013).*

(Continued)

*Primary Examiner* — Navin Natnithithadha
*Assistant Examiner* — Andrey Shostak
(74) *Attorney, Agent, or Firm* — Shumaker & Sieffert, P.A.

(57) ABSTRACT

A method for monitoring autoregulation includes, using a processor, receiving a blood pressure signal, a regional oxygen saturation signal, and a blood volume signal from a patient. The method also includes determining a first linear correlation between the blood pressure signal and the regional oxygen saturation signal and determining a second linear correlation between the blood pressure signal and the blood volume signal. The method also includes determining a confidence level associated with the first linear correlation based at least in part on the second linear correlation and providing a signal indicative of the patient's autoregulation status to an output device based on the linear correlation and the confidence level.

19 Claims, 6 Drawing Sheets

(51) Int. Cl.

| | |
|---|---|
| A61B 5/0205 | (2006.01) |
| A61B 5/1455 | (2006.01) |
| A61B 5/145 | (2006.01) |
| A61B 5/021 | (2006.01) |

(52) U.S. Cl.
CPC .......... *A61B 5/14551* (2013.01); *A61B 5/021* (2013.01); *A61B 5/14546* (2013.01)

(56) References Cited

U.S. PATENT DOCUMENTS

| | | | |
|---|---|---|---|
| 5,482,034 A | 1/1996 | Lewis et al. | |
| 5,533,507 A | 7/1996 | Potratz | |
| 5,577,500 A | 11/1996 | Potratz | |
| 5,584,296 A | 12/1996 | Cui et al. | |
| 5,626,140 A | 5/1997 | Feldman et al. | |
| 5,803,910 A | 9/1998 | Potratz | |
| 5,934,277 A | 8/1999 | Mortz | |
| 6,385,471 B1 | 5/2002 | Mortz | |
| 6,438,399 B1 | 8/2002 | Kurth | |
| 6,453,183 B1 | 9/2002 | Walker | |
| 6,505,060 B1 | 1/2003 | Norris | |
| 6,510,329 B2 | 1/2003 | Heckel | |
| 6,599,251 B2 | 7/2003 | Chen et al. | |
| 6,668,182 B2 | 12/2003 | Hubelbank | |
| 6,714,803 B1 | 3/2004 | Mortz | |
| 6,754,516 B2 | 6/2004 | Mannheimer | |
| 6,896,661 B2 | 5/2005 | Dekker | |
| 6,987,994 B1 | 1/2006 | Mortz | |
| 7,001,337 B2 | 2/2006 | Dekker | |
| 7,221,969 B2 | 5/2007 | Stoddart et al. | |
| 7,268,873 B2 | 9/2007 | Sevick-Muraca et al. | |
| 7,744,541 B2 | 6/2010 | Baruch et al. | |
| 8,556,811 B2 | 10/2013 | Brady | |
| 2004/0097797 A1 | 5/2004 | Porges et al. | |
| 2005/0004479 A1 | 1/2005 | Townsend et al. | |
| 2005/0033129 A1 | 2/2005 | Edgar, Jr. et al. | |
| 2005/0192488 A1 | 9/2005 | Bryenton et al. | |
| 2005/0192493 A1 | 9/2005 | Wuori | |
| 2007/0004977 A1 | 1/2007 | Norris | |
| 2007/0049812 A1 | 3/2007 | Aoyagi et al. | |
| 2008/0081974 A1 | 4/2008 | Pav | |
| 2008/0146901 A1 | 6/2008 | Katura et al. | |
| 2008/0200785 A1 | 8/2008 | Fortin | |
| 2008/0228053 A1 | 9/2008 | Wang et al. | |
| 2009/0326386 A1 | 12/2009 | Sethi et al. | |
| 2010/0010322 A1* | 1/2010 | Brady ................ | A61B 5/02028 600/301 |
| 2010/0030054 A1 | 2/2010 | Baruch et al. | |
| 2010/0049082 A1 | 2/2010 | Hu et al. | |
| 2011/0046459 A1 | 2/2011 | Zhang et al. | |
| 2011/0098933 A1* | 4/2011 | Ochs ................ | A61B 5/14551 702/19 |
| 2011/0105912 A1 | 5/2011 | Widman et al. | |
| 2012/0054331 A1* | 3/2012 | Dagan ................ | G06F 11/0712 709/224 |
| 2012/0149994 A1 | 6/2012 | Luczyk et al. | |
| 2012/0232416 A1* | 9/2012 | Gilham ................ | A61B 5/7246 600/515 |
| 2012/0253211 A1 | 10/2012 | Brady et al. | |
| 2012/0271130 A1 | 10/2012 | Benni | |
| 2013/0190632 A1 | 7/2013 | Baruch et al. | |
| 2014/0073888 A1* | 3/2014 | Sethi ...................... | A61B 5/021 600/324 |
| 2014/0275818 A1 | 9/2014 | Kassem et al. | |
| 2014/0278285 A1 | 9/2014 | Marmarelis et al. | |
| 2016/0106372 A1 | 4/2016 | Addison et al. | |
| 2016/0324425 A1 | 11/2016 | Addison et al. | |
| 2016/0345913 A1 | 12/2016 | Montgomery et al. | |
| 2017/0000395 A1 | 1/2017 | Addison et al. | |
| 2017/0000423 A1 | 1/2017 | Addison et al. | |
| 2017/0095161 A1 | 4/2017 | Addison et al. | |
| 2017/0105631 A1 | 4/2017 | Addison et al. | |
| 2017/0105672 A1 | 4/2017 | Addison et al. | |

FOREIGN PATENT DOCUMENTS

| | | |
|---|---|---|
| WO | WO0059374 | 10/2000 |
| WO | WO03000125 A1 | 1/2003 |
| WO | WO03071928 A2 | 9/2003 |
| WO | WO2004075746 A2 | 9/2004 |
| WO | WO2008097411 A1 | 8/2008 |
| WO | 2012156826 A2 | 11/2012 |
| WO | 2016061239 A1 | 4/2016 |
| WO | WO2016182853 A1 | 11/2016 |

OTHER PUBLICATIONS

Lee, Jennifer K., et al. "Cerebrovascular autoregulation in pediatric moyamoya disease." Pediatric Anesthesia 23.6 (2013): 547-556 (Year: 2013).*

Massart, Desire L., et al. "Least median of squares: a robust method for outlier and model error detection in regression and calibration." Analytica Chimica Acta 187 (1986): 171-179 (Year: 1986).*

Chuan et al., "Is cerebrovascular autoregulation associated with outcomes after major noncardiac surgery? A prospective observational pilot study," Acta Anaesthesiol Scand., Aug. 5, 2018, 10 pp.

Wu, Dongmei, et al.; "Na*/H* Exchange inhibition delays the onset of hypovolemic circulatory shock in pigs," SHOCK, vol. 29, No. 4, pp. 519-525 (2008).

Wu, et al.; "Using synchrosqueezing transform to discover breathing dynamics from ECG signals," arXiv:1105.1571, vol. 2, Dec. 2013, pp. 1-9.

Wu, Hau-tieng, et al.; "Evaluating physiological dynamics via Synchrosqueezing: Prediction of Ventilator Weaning," Journal of Latex Class Files, vol. 11, No. 4, Dec. 2012, pp. 1-9.

Zhang, Rong, et al.; "Transfer function analysis of dynamic cerebral autoregulation in humans," 1998 the American Physiological Society; pp. H233-H241.

Zweifel, Christian, et al.; "Continuous time-domain monitoring of cerebral autoregulation in neurocritical care," Medical Engineering & Physics, Elsevier Ltd., vol. 36, No. 5, 2014, pp. 638-645.

International Search Report and Written Opinion of International Application No. PCT/US2017/036598, dated Sep. 12, 2017, 18 pp.

Addison et al., "A Review of Wavelet Transform Time-Frequency Methods for NIRS-Based Analysis of Cerebral Autoregulation," IEEE Reviews in Biomedical Engineering, vol. 8, May 22, 2015, 8 pp.

Larson et al., "Cerebrovascular autoregulation after rewarming from hypothermia in a neonatal swine model of asphyxic brain injury," Cerebral Autoregulation, Hypothermia, and Asphyxia, American Physiological Society, Sep. 5, 2013, 10 pp.

Lee et al., "Cerebrovascular Autoregulation in Pediatric Moyamoya Disease," Paediatric Anesthesia, ISSN 1155-5645, Mar. 18, 2013, 10 pp.

Lee et al., "Cerebral Blood Flow and Cerebrovascular Autoregualtion in a Swine Model of Pediatric Cardiac Arrest and Hypothermia," NIH Public Access, Oct. 2011, 22 pp.

Reinhard et al., "Cerebral Autoregulation in Carotid Artery Occlusive Disease Assessed From Spontaneous Blood Pressure Fluctuations by the Correlation Coefficient Index," published Aug. 14, 2003, 8 pages.

U.S. Appl. No. 15/666,167, filed Aug. 1, 2017, naming inventors Addison et al.

Addison, P. S., et al.; "Low-Oscillation Complex Wavelets," Journal of Sound and Vibration, 2002, vol. 254, Elsevier Science Ltd., pp. 1-30.

Addison, P. S.; "The Illustrated Wavelet Transform Handbook," 2002, IOP Publishing Ltd., Bristol, UK, Ch. 2.

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Barreto, Armando B., et al.; "Adaptive LMS Delay Measurement in dual Blood Volume Pulse Signals for Non-Invasive Monitoring," *IEEE*, pp. 117-120 (1997).

(56) References Cited

OTHER PUBLICATIONS

Bassan, Haim, et al.; "Identification of pressure passive cerebral perfusion and its mediators after infant cardiac surgery," Pediatric Research Foundation, vol. 57, No. 1, 2005; pp. 35-41.

Belal, Suliman Yousef, et al.; "A fuzzy system for detecting distorted plethysmogram pulses in neonates and paediatric patients," Physiol. Meas., vol. 22, pp. 397-412 (2001).

Brady, Ken M., et al.; "Continuous Measurement of Autoregulation by Spontaneous Fluctuations in Cerebral Perfusion Pressure Comparison of 3 Methods," NIH Public Access Author Manuscript, Stroke, 2008, 39(9), pp. 1-13.

Brady, Ken M., et al.; "Continuous time-domain analysis of cerebrovascular autoregulation using near-infrared spectroscopy," American Stroke Association, DOI:10.1161/strokeaha.107.485706, Aug. 2007, pp. 2818-2825.

Brady, Ken M., et al.; "Monitoring cerebral blood flow pressure autoregulation in pediatric patients during cardiac surgery," Stroke 2010;41:1957-1962 (http://stroke.ahajournals.org/content/41/9/1957.full).

Brady, Ken M., et al.; "Noninvasive Autoregulation Monitoring with and without Intracranial Pressure in a Naïve Piglet Brain," Neuroscience in Anesthesiology and Perioperative Medicine, 2010, vol. 111, No. 1, International Anesthesia Research Society, pp. 191-195.

Brady, Kenneth, et al.; "Real-Time Continuous Monitoring of Cerebral Blood Flow Autoregulation Using Near-Infrared Spectroscopy in Patients Undergoing Cardiopulmonary Bypass," Stroke, 2010, 41, American Heart Association, Inc., pp. 1951-1956.

Caicedo, Alexander, et al.; "Cerebral Tissue Oxygenation and Regional Oxygen Saturation Can be Used to study Cerebral Autoregulation in Prematurely Born Infants," Pediatric Research, vol. 69, No. 6, Jun. 1, 2011, pp. 548-553.

Caicedo, Alexander, et al.; "Detection of cerebral autoregulation by near-infrared spectroscopy in neonates: performance analysis of measurement methods," Journal of Biomedical Optics 17 (11) pp. 117003-1-117003-9 (Nov. 2012).

Chan, K.W., et al.; "17.3: Adaptive Reduction of Motion Artifact from Photoplethysmographic Recordings using a Variable Step-Size LMS Filter," IEEE, pp. 1343-1346 (2002)+A10.

Chen, Li, et al.; "The role of pulse oximetry plethysmographic waveform monitoring as a marker of restoration of spontaneous circulation: a pilot study," Chin Crit Care Med, 2015, vol. 27, No. 3, pp. 203-208.

Chen, Liangyou, et al.; "IS respiration-induced variation in the photoplethysmogram associated with major hypovolemia in patients with actue tramatic injuries," SHOCK, vol. 34, No. 5, pp. 455-460 (2010).

Cheng, Ran, et al.; "Noninvasive optical evaluation of spontaneous low frequency oscillations in cerebral hemodynamics", Neuroimage, Academic Press, vol. 62, No. 3, May 24, 2012, pp. 1445-1454.

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Cysewska-Sobusaik, Anna; "Metrological Problems With noninvasive Transillumination of Living Tissues," *Proceedings of SPIE*, vol. 4515, pp. 15-24 (2001).

Czosnyka, Marek, et al.; "Monitoring of cerebrovascular autoregulation: Facts, Myths, and Missing Links," Neurocrit Care (2009) 10:373-386.

Daubechies, Ingrid, et al.; "A Nonlinear Squeezing of the Continuous Wavelet Transform Based on Auditory Nerve Models," Princeton University, 1996, Acoustic Processing Department, NY, pp. iii, 1-17.

Daubechies, Ingrid, et al.; "Synchrosqueezed Wavelet Transforms: an Empirical Mode Decomposition-like Tool," Princeton University, 2010, Applied and Computational Harmonic Analysis, pp. 1-32.

Dias, Celeste, et al.; "Optimal Cerebral Perfusion Pressure Management at Bedside: A Single-Center Pilot Study," Neurocritical care, vol. 23, No. 1, Jan. 8, 2015; pp. 92-102; ISSN: 1541-6933.

East, Christine E., et al.; "Fetal Oxygen Saturation and Uterine Contractions During Labor," *American Journal of Perinatology*, vol. 15, No. 6, pp. 345-349 (Jun. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engie in Medicine and Biology Society*, vol. 20, No. 6, p. 3072-3075, 1998.

Eichhorn, Lars, et al.; "Evaluation of newar-infrared spectroscopy under apnea-dependent hypoxia in humans," Journal of Clinical Monitoring and Computing, vol. 29, No. 6, Feb. 4, 2015, pp. 749-757.

Gao, Yuanjuin, et al.; "Response of cerebral tissue oxygenation and arterial blood pressure to postural change assessed by wavelet phase coherence analysis", 2014 7th International conference on Biomedical Engineering and Informatics, IEEE, Oct. 14, 2014, pp. 373-377.

Ge, Z.; "Significance tests for the wavelet cross spectrum and wavelet linear coherence," Annales Geophysicae, 2008, 26, Copernicus Publications on behalf of European Geosciences Union, pp. 3819-3829.

Gesquiere, Michael J., et al., "Impact of withdrawal of 450 ML of blook on respiration-induced oscillations of the ear plethysmographic waveform," Journal of Clinical Monitoring and Computing (2007) 21:277-282.

Goldman, Julian M.; "Masimo Signal Extraction Pulse Oximetry," *Journal of Clinical Monitoring and Computing*, vol. 16, pp. 475-483 (2000).

Gommer, Erik D., et al.; "Dynamic cerebral autoregulation: different signal processing methods without influence on results and reproducibility"; Medical & Biological Engineering & Computer; vol. 48, No. 12, Nov. 4, 2010; pp. 1243-1250.

Hamilton, Patrick S., et al.; "Effect of Adaptive Motion-Artifact Reduction on QRS Detection," *Biomedical Instrumentation & Technology*, pp. 197-202 (May-Jun. 2000).

Huang, J., et al.; "Low Power Motion Tolerant Pulse Oximetry," Anesthesia & Analgesia 2002 94: S103.

Johansson, A.; "Neural network for photoplethysmographic respiratory rate monitoring," *Medical & Biological Engineering & Computing*, vol. 41, pp. 242-248 (2003).

Kaestle, S.; "Determining Artefact Sensitivity of New Pulse Oximeters in Laboratory Using Signals Obtained from Patient," *Biomedizinische Technik*, vol. 45 (2000).

Kim, J.M., et al.; "Signal Processing Using Fourier & Wavelet Transform for pulse oximetry," pp. II-310-II-311 (2001).

Kirkham, S.K., et al.; "A new mathematical model of dynamic cerebral autoregulation based on a flow dependent feedback mechanism; Dynamic cerebral autoregulation modelling," Physiological Measurement, Institute of Physics Publishing, vol. 22, No. 3, Aug. 1, 2001; (13 pgs.).

Leahy, Martin J., et al.; "Sensor Validation in Biomedical Applications," *IFAC Modelling and Control in Biomedical Systems*, Warwick, UK; pp. 221-226 (1997).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Lee, Jennifer K., et al.; A pilot study of cerebrovascular reactivity autoregulation after pediatric cardiac arrest, Resuscitation 85, 2014, Elsevier Ireland Ltd., pp. 1387-1393.

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Massart, Desire L., et al.; "Least Median of Squares: A Robust Method for Outlier and Model Error Detection in Regression and

(56) References Cited

OTHER PUBLICATIONS

Calibration," Analytica Chimica Acta, 1986, Elsevier Science Publishers B.V., The Netherlands, pp. 171-179.

McGrath, S.P., et al.; "Pulse oximeter plethysmographic waveform changes in awake, spontaneously breathing, hypovolemic volunteers," Anesth. Analg. vol. 112 No. 2, pp. 368-374 (2010).

Montgomery, Dean, et al.; "Data cluestering methods for the determination of cerebral autoregulation functionality," Journal of Clinical Monitoring and Computing, vol. 30, No. 5, Sep. 16, 2015, pp. 661-668.

Morren, G., et al.; "Detection of autoregulation in the brain of premature infants using a novel subspace-based technique," 23rd Annual International Conference of IEEE Engineering in Medicine and Biology Society, Oct. 2001; pp. 1-4.

Morren, Geert, et al.; "Quantitation of the concordance between cerebral intravascular oxygenation and mean arterial blood pressure for the detection of impaired autoregulation," 29th Annual Meeting of the International Society on Oxygen Transport to Tissue, UofP, Aug. 2001; pp. 1-5.

Neumann, R., et al.; "Fourier Artifact suppression Technology Provides Reliable $SpO_2$," Anesthesia & Analgesia 2002, 94: S105.

Obrig, Hellmuth, et al.; "Spontaneous low frequency oscillations of cerebral heodynamics and metabolism in human adults," NeuroImage 12, 623-639 (2000).

Odagiri, Y.; "Pulse Wave Measuring Device," *Micromechatronics*, vol. 42, No. 3, pp. 6-11 (published Sep. 1998) (Article in Japanese—contains English summary of article).

Ono, Masahiro, et al.; "Validation of a stand-alone near-infrared spectroscopy system for monitoring cerebral autoregulaiton during cardiac surgery," International Anethesia Research Society, Jan. 2013, vol. 116, No. 1, pp. 198-204.

Panerai, B.; "Cerebral Autoregulation: from models to clinical Applications," Cardiovascular Engineering: an International Journal, vol. 8, No. 1, Nov. 28, 2007, (28 pgs.).

Payne, Stephen J., et al.; "Tissue Oxygenation Index as a Measure of Cerebral Autoregulation," Biomedial Engineering, Feb. 2004, Innsbruck, Austria, pp. 546-550.

Reinhard, Matthias, et al.; "Spatial mapping of dynamic cerebral autoregulation by multichannel near-infrared spectrosccopy in high-grade carotid artery disease", International Society for optical Engineering, SPIE, vol. 19, No. 9, Sep. 1, 2014, p. 97005.

Reinhard, Matthias, et al.; "Oscillatory cerebral hemodynamics—the macro- vs. microvascular level," Journal of the Neurological Sciences 250 (2006) 103-109.

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Rowley, A.B., et al.; "Synchronization between arterial blood pressure and cerebral oxyhaemoglobin concentration investigated by wavelet cross-correlation," Physiol. Meas., vol. 28, No. 2, Feb. 2007, pp. 161-173.

Shamir, M., et al.; "Pulse oximetry plethysmographic waveform during changes in blood volume," British Journal of Anaesthesia 82(2): 178-81 (1999).

Sorensen, Henrik, et al.; "A note on arterial to venous oxygen saturation as reference for NIRS-determined frontal lobe oxygen saturation in healthy humans," Frontiers in Physiology, vol. 4, Art. 403, Jan. 2014, pp. 1-3.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Such, Hans Olaf; "Optoelectronic Non-invasive Vascular Diagnostics Using multiple Wavelength and Imaging Approach," *Dissertation*, (1998).

Todd, Bryan, et al.; "The Identification of Peaks in Physiological Signals," *Computers and Biomedical Research*, vol. 32, pp. 322-335 (1999).

Tsuji, Miles, et al.; "Cerebral intravascular oxygenation correlates with mean arterial pressure in critically ill premature infants," American Academy of Pediatrics, 2000; 106; pp. 625-632.

Wagner, Bendicht P., et al.; "Dynamic cerebral autoregulatory response to blood pressure rise measured by near-infrared spectroscopy and intracranial pressure," Critical Care Medicine 2002, vol. 30, No. 9, pp. 2014-2021.

Whitaker, E., et al.; "Cerebrovascular Autoregulation After Pediatric Cardiac Arrest," NEURO—85, 2012, 2 pgs.

Williams, Monica, et al.; "Intraoperative blood pressure and Cerebral perfusion: strategies to clarify hemodynamic goals," Paediatric Anaesthesia, vol. 24, No. 7, Jul. 12, 2014; pp. 657-667; XP055331904.

Wong, Flora Y., et al.; "Impaired Autoregulation in preterm infants identified by using spatially resolved spectroscopy," American Academy of Pediatrics DOI:10.1542 (2008) e604-611.

U.S. Appl. No. 15/648,665, filed Jul. 13, 2017, Dean Montgomery.

* cited by examiner

US 10,932,724 B2

SYSTEMS AND METHODS FOR MONITORING AUTOREGULATION USING A CONFIDENCE LEVEL

CROSS-REFERENCE TO RELATED APPLICATIONS

The present application claims the benefit of U.S. Provisional Application No. 62/181,067, which was filed on Jun. 17, 2015, and entitled "SYSTEMS AND METHODS FOR REDUCING SIGNAL NOISE WHEN MONITORING AUTOREGULATION", the disclosure of which is incorporated herein by reference in its entirety.

BACKGROUND

The present disclosure relates generally to medical devices and, more particularly, to systems and methods for monitoring autoregulation.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, medical professionals often desire to monitor certain physiological parameters of their patients. In some cases, clinicians may wish to monitor a patient's autoregulation. Autoregulation is a physiological process that attempts to maintain an optimal cerebral blood flow to supply appropriate levels of oxygen and nutrients to the brain. During autoregulation, cerebral arterioles dilate or constrict to maintain optimal blood flow. For example, as cerebral pressure decreases, cerebral arterioles dilate in an attempt to maintain blood flow. As cerebral pressure increases, cerebral arterioles constrict to reduce the blood flow that could cause injury to the brain. If the patient's autoregulation process is not functioning properly, the patient may experience inappropriate cerebral blood flow, which may have negative effects on the patient's health. In particular, a drop in cerebral blood flow may cause ischemia, which may result in tissue damage or death of brain cells. An increase in cerebral blood flow may cause hyperemia, which may result in swelling of the brain or edema.

Some existing systems for monitoring autoregulation may determine a patient's autoregulation status based on various physiological values. Such physiological values may be subject to various sources of error, such as noise caused by motion, operator error, poor quality measurements, drugs, or other anomalies. However, existing systems for monitoring autoregulation may not reduce the various sources of error when utilizing the measured physiological values to determine the patient's autoregulation status. Furthermore, existing systems may not determine and/or utilize a reliable metric to determine whether the autoregulation status calculated from the physiological values is reliable. Accordingly, the autoregulation status determined by such existing systems may be inaccurate or unreliable.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
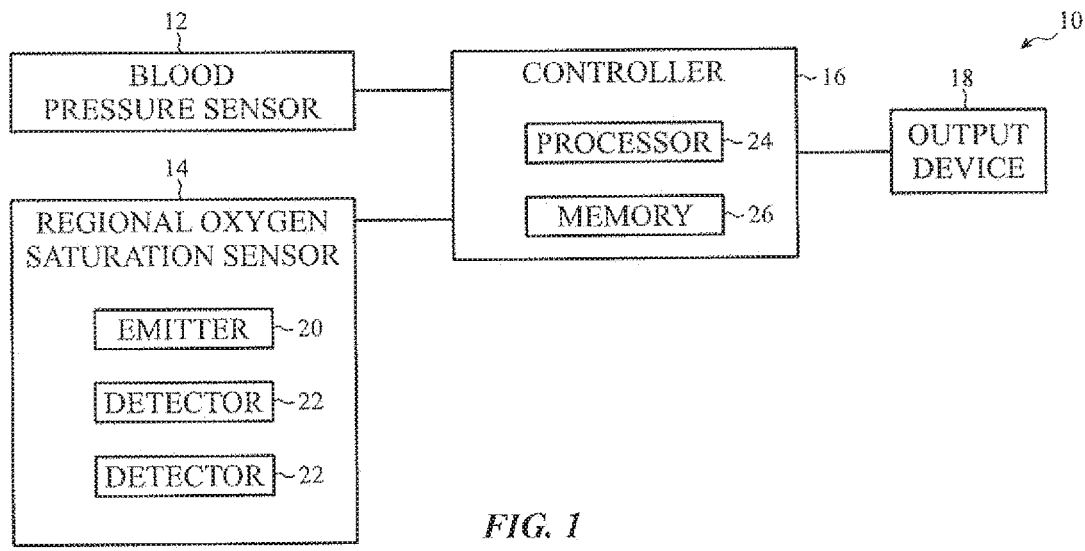
FIG. 1 is a block diagram of an embodiment of a system for monitoring autoregulation of a patient.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A physician may monitor a patient's autoregulation through the use of various monitoring devices and systems that measure various physiological parameters. In certain embodiments of the present disclosure, a patient's autoregulation may be monitored by correlating measurements of the patient's blood pressure (e.g., arterial blood pressure) with measurements of the patient's oxygen saturation (e.g., regional oxygen saturation). In particular, a cerebral oximetry index (COx) may be derived based at least in part on a linear correlation between the patient's blood pressure and oxygen saturation. In addition, in certain embodiments of the present disclosure, the patient's autoregulation may be monitored by correlating measurements of the patient's blood pressure with measurements of the patient's blood volume (e.g., blood volume proxy). In particular, a hemoglobin volume index (HVx) may be derived based at least in part on a linear correlation between the patient's blood pressure and blood volume. While features of the present disclosure are discussed with reference to COx and HVx, it should be noted that in other embodiments, various other linear correlations may be determined to help evaluate a patient's autoregulation. For example, a linear correlation between measurements of a patient's blood pressure and measurements of a patient's cerebral blood flow may derive a mean velocity index (Mx). As a further example, a linear correlation between measurements of a patient's blood pressure and measurements of a patient's intracranial pressure may derive a pressure reactivity index (PRx). In certain situations, these indexes may be utilized to determine or help evaluate a patient's autoregulation.

The disclosed systems and methods may determine linear correlations between the measured physiological parameters using regression analyses. For example, the system may be configured to apply a least median of squares (LMS) regression method or a least trimmed squares regression method (LTS) to oxygen saturation measurements plotted against blood pressure measurements to determine a regression line associated with COx. As noted above, during patient monitoring, physiological values may be affected by noise. These regression methods may enable the system to ignore or exclude data outliers representative of the noise, and to utilize the remaining data to determine the COx or HVx. Accordingly, the calculated COx or HVx may have less variability due to signal noise and may be less susceptible to data outliers. In certain embodiments, the system may evaluate the quality of the data with one or more quality metrics in order to determine which portions of the data are included or excluded from the regression methods.

Further, the disclosed systems and methods may determine a confidence metric in order to determine the reliability of the calculated COx or HVx. Existing systems and methods may determine a significance value (p value) related to the COx to determine whether the portions of the calculated COx are reliable or unreliable. In the disclosed systems and methods, it may be beneficial to determine the reliability of the COx or HVx based on a confidence metric. For example, in certain embodiments, the system may utilize HVx as a confidence metric for COx, or COx as a confidence metric for HVx, as further described below. In certain embodiments, the system may determine the confidence metric based on a combination parameter, which may be calculated as the mean or weighted average of the COx and HVx. In addition, in certain embodiments, the system may determine the confidence metric based on a linear correlation confidence coefficient, which may be calculated by correlating the COx with the HVx. Accordingly, the system may utilize the confidence metric to evaluate the reliability of the calculated COx or HVx, which may be used to accurately monitor the patient's autoregulation.

In addition, the disclosed systems and methods may be configured to calculate COx or HVx over a correlation window having a particular period (e.g., length measured in seconds). For example, a correlation window having a particular period may incrementally scan a continuous signal representative of the oxygen saturation measurements plotted against the blood pressure measurements to calculate the COx. The correlation window may have a period of 100 seconds, 150 seconds, 200 seconds, 250 seconds, 300 seconds, 350 seconds, 400 seconds, and so forth. In certain embodiments, such as in situations where the confidence metric evaluates a low reliability of the autoregulation status, the system may be configured to dynamically vary the period of the correlation window to compute or recompute the COx or HVx. In certain embodiments, a user or operator may manually select or vary the period of the correlation window to compute or recompute the COx or HVx. Varying the period of the correlation window allows the system to exclude or ignore portions of the COx or HVx with high variability, thereby improving the reliability of the COx or HVx, which may be used to accurately monitor the patient's autoregulation Accordingly, the system may be configured to exclude or ignore data caused by noise when calculating the COx or HVx to improve the reliability of the COx or HVx. Further, the system may determine a confidence metric to evaluate the reliability of the COx or HVx. In this manner, the system may be configured to accurately and reliably monitor autoregulation of a patient for a medical professional, as discussed in more detail below.

FIG. 1 illustrates an embodiment of a system 10 for monitoring an autoregulation of a patient. As shown, the system 10 includes a blood pressure sensor 12, an oxygen saturation sensor 14 (e.g., a regional oxygen saturation sensor), a controller 16, and an output device 18. As further described in detail below, the blood pressure sensor 12 may be any sensor or device configured to obtain the patient's blood pressure (e.g., arterial blood pressure). The oxygen saturation sensor 14 may be any sensor or device configured to obtain the patient's oxygen saturation signal indicative of blood oxygen saturation within one or more regions of the patient. The oxygen saturation sensor 14 and the blood pressure sensor 12 may also determine various other physiological parameters from the patient, such as blood volume or blood volume proxy, cerebral blood flow, intracranial pressure, or other types of information that may be useful to determine a patient's autoregulation status. The controller 16 may be configured to gather physiological signals measured by the sensors (e.g., blood pressure sensor 12, regional oxygen saturation sensor 14, etc.) to evaluate the patient's autoregulation, and may be configured to output information related to the autoregulation status to the output device 18.

In certain embodiments, the blood pressure sensor 12 may include a blood pressure cuff for non-invasively monitoring blood pressure or an arterial line for invasively monitoring blood pressure. In certain embodiments, the blood pressure sensor 12 may include one or more pulse oximetry sensors. In some such cases, the patient's blood pressure may be derived by processing time delays between two or more characteristic points within a single plethysmography (PPG) signal obtained from a single pulse oximetry sensor. Various techniques for deriving blood pressure based on a comparison of time delays between certain components of a single PPG signal obtained from a single pulse oximetry sensor is described in U.S. Publication No. 2009/0326386, entitled "Systems and Methods for Non-Invasive Blood Pressure Monitoring," the entirety of which is incorporated herein by reference. In other cases, the patient's blood pressure may be continuously, non-invasively monitored via multiple pulse oximetry sensors placed at multiple locations on the patient's body. As described in U.S. Pat. No. 6,599,251, entitled "Continuous Non-invasive Blood Pressure Monitoring Method and Apparatus," the entirety of which is incorporated herein by reference, multiple PPG signals may be obtained from the multiple pulse oximetry sensors, and the PPG signals may be compared against one another to estimate the patient's blood pressure. Regardless of its form, the blood pressure sensor 12 may be configured to generate a blood pressure signal indicative of the patient's blood pressure (e.g., arterial blood pressure) over time. As discussed in more detail below, the blood pressure sensor 12 may provide the blood pressure signal to the controller 16 or to any other suitable processing device to enable evaluation of the patient's autoregulation status.

As shown, the oxygen saturation sensor 14 may be a regional oxygen saturation sensor configured to generate an oxygen saturation signal indicative of blood oxygen saturation within the venous, arterial, and capillary systems within a region of the patient. For example, the oxygen saturation sensor 14 may be configured to be placed on the patient's forehead and may be used to calculate the oxygen saturation of the patient's blood within the venous, arterial, and capillary systems of a region underlying the patient's forehead (e.g., in the cerebral cortex).

In such cases, the oxygen saturation sensor 14 may include an emitter 20 and multiple detectors 22. The emitter 20 may include at least two light emitting diodes (LEDs), each configured to emit at different wavelengths of light, e.g., red or near infrared light. In one embodiment, the LEDs of the emitter 20 emit light in the range of about 600 nm to about 1000 nm. In a particular embodiment, one LED of the emitter 20 is configured to emit light at about 730 nm and the other LED of the emitter 20 is configured to emit light at about 810 nm. One of the detectors 22 is positioned relatively "close" (e.g., proximal) to the emitter 20 and one of the detectors 22 is positioned relatively "far" (e.g., distal) from the emitter 22. Light intensity of multiple wavelengths may be received at both the "close" and the "far" detectors 22. For example, if two wavelengths are used, the two wavelengths may be contrasted at each location and the resulting signals may be contrasted to arrive at a regional saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). Surface data from the skin and skull may be subtracted out, to generate a regional oxygen saturation ($rSO_2$) signal for the target tissues over time. In certain embodiments, an isosbestic wavelength and/or an isosbestic point on the wavelengths may be utilized to extract information related to blood volume and generate a blood volume signal for the patient over time. As discussed in more detail below, the oxygen saturation sensor 14 may provide the regional oxygen saturation signal and/or the blood volume signal to the controller 16 or to any other suitable processing device to enable evaluation of the patient's autoregulation status.

In operation, the blood pressure sensor 12 and the oxygen saturation sensor 14 may each be placed on the same or different parts of the patient's body. Indeed, the blood pressure sensor 12 and the oxygen saturation sensor 14 may in some cases be part of the same sensor or supported by a single sensor housing. For example, the blood pressure sensor 12 and the oxygen saturation sensor 14 may be part of an integrated oximetry system configured to non-invasively measure blood pressure (e.g., based on time delays in a PPG signal) and regional oxygen saturation. One or both of the blood pressure sensor 12 or the oxygen saturation sensor 14 may be further be configured to measure other parameters over time, such as blood volume or blood volume proxy, cerebral blood flow, intracranial pressure, hemoglobin, respiratory rate, respiratory effort, heart rate, saturation pattern detection, response to stimulus such as bispectral index (BIS) or electromyography (EMG) response to electrical stimulus, or the like. In certain embodiments, other types of sensors or monitoring techniques (e.g., photoacoustic spectroscopy) may be used to determine these physiological parameters over time. While an exemplary system 10 is shown, the exemplary components illustrated in FIG. 1 are not intended to be limiting. Indeed, additional or alternative components and/or implementations may be used.

In certain embodiments, the blood pressure sensor 12 and the oxygen saturation sensor 14 may be configured to provide the oxygen saturation signal, the blood pressure signal, and a blood volume signal to the controller 16. In certain embodiments, the controller 16 is an electronic controller having electrical circuitry configured to process the various received signals. In particular, the controller 16 may be configured to process the blood pressure signal, the oxygen saturation signal, and the blood volume signal to evaluate the patient's cerebral autoregulation status. Although the blood pressure sensor 12 and the oxygen saturation sensor 14 may be configured to provide their respective signals or data directly to the controller 16, in certain embodiments, the signals or data obtained by the blood pressure sensor 12 and/or the oxygen saturation sensor 14 may be provided to one or more intermediate processing devices (e.g., specialized monitor, such as a blood pressure monitor or an oxygen saturation monitor, or the like), which may in turn provide processed signals or data to the controller 16.

As discussed in more detail below, the controller 16 may be configured to determine a cerebral oximetry index (COx) based on the blood pressure signal and the oxygen saturation signal. Further, in some embodiments, the controller 16 may be configured to determine a hemoglobin volume index (HVx) based on the blood pressure signal and the blood volume signal. The COx is indicative of vascular reactivity, which is related to cerebral blood vessels' ability to control proper blood flow, via vasoconstriction (a narrowing of the blood vessel) and/or vasodilation (expansion of the blood vessel), for example. The HVx is indicative of pressure reactivity, which is related to cerebral blood vessels' ability to control proper intracranial pressure, for example. Thus, COx and HVx may also be indicative of whether the patient's autoregulation is impaired, and one or more of these parameters may be utilized to evaluate a patient's autoregulation status.

The controller 16 may derive the COx in part by determining a linear correlation between blood pressure measurements and oxygen saturation measurements. Likewise, the controller 16 may derive the HVx in part by determining a linear correlation between blood pressure measurements and blood volume measurements. Specifically, the controller 16 may be configured to determine COx by applying one or more regression techniques (e.g., least medium of square (LMS), least trimmed squares (LTS)) to the oxygen saturation measurements plotted against the blood pressure measurements and determine HVx by applying one or more regression techniques to the blood volume measurements plotted against the blood pressure measurements, as further described with respect to FIGS. 3A-4B. The result of applying these regression techniques is a regression line between the physiological measurements that ignore or exclude data outliers indicative of noise within the received signals. Accordingly, the resulting COx or HVx may exhibit less variability due to signal noise and may be more stable and reliable. The controller 16 may be configured to determine the patient's autoregulation status based on the regression lines that are associated with the COx and the HVx. For example, in certain embodiments, the controller 16 may determine a slope of the regression line associated with the COx, which may be between −1 and +1, inclusive, where 1 represents total negative correlation, +1 represents total positive correlation, and 0 represents the absence of correlation between the blood pressure measurements and the oxygen saturation measurements. Thus, COx values between −1 and 0 may suggest that cerebral autoregulation is working properly, while COx values between 0 and 1 may suggest that the cerebral autoregulation is impaired. In some cases, a predetermined threshold between 0 and 1 may be utilized to determine whether the patient's autoregulation is impaired. For example, in some embodiments, the controller 16 may be configured to determine that the patient's autoregulation is impaired when the COx value is greater than 0.1, 0.2, 0.3, 0.4, 0.5, 0.6, 0.7, 0.8, or 0.9. Accordingly, the controller 16 may be configured to determine the COx value and/or the patient's autoregulation status based on the linear correlation between the blood pressure measurements and oxygen saturation measurements obtained by the blood pressure sensor 12 and the oxygen saturation sensor 14, respectively. Likewise, the controller 16 may be configured to determine the HVx value and/or the patient's autoregulation status based on the linear correlation between the blood volume measurements and the blood pressure measurements.

Figure 5:
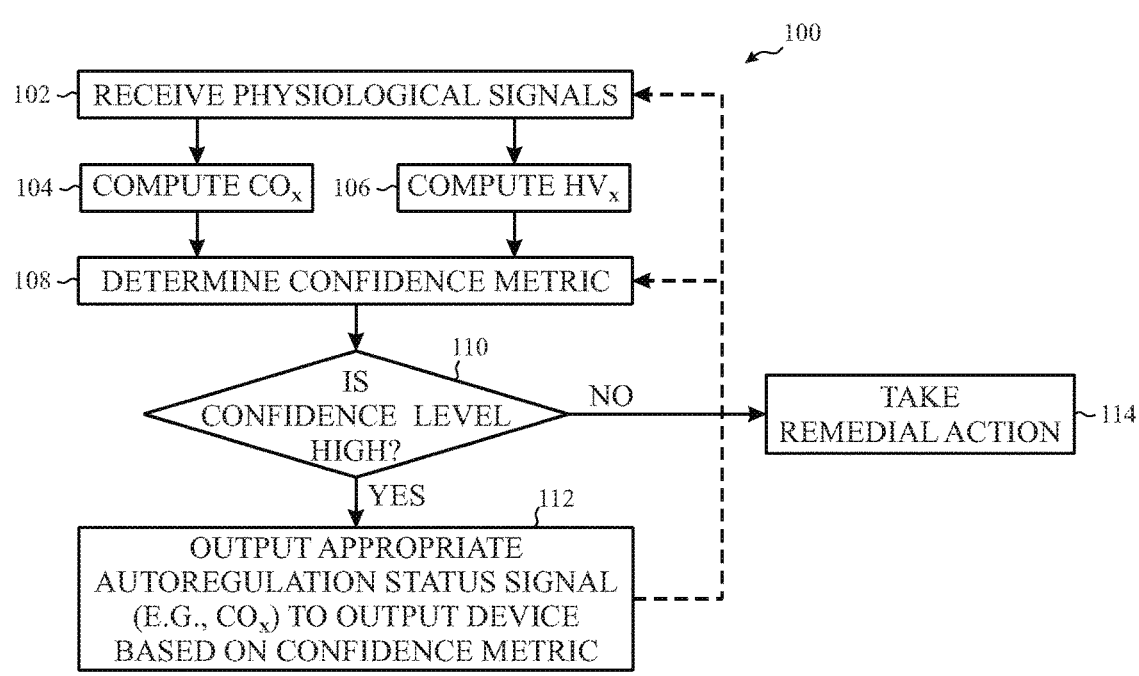
FIG. 5 is a process flow diagram of a method of monitoring autoregulation based on a confidence metric, in accordance with an embodiment.
Figures 6, 7:
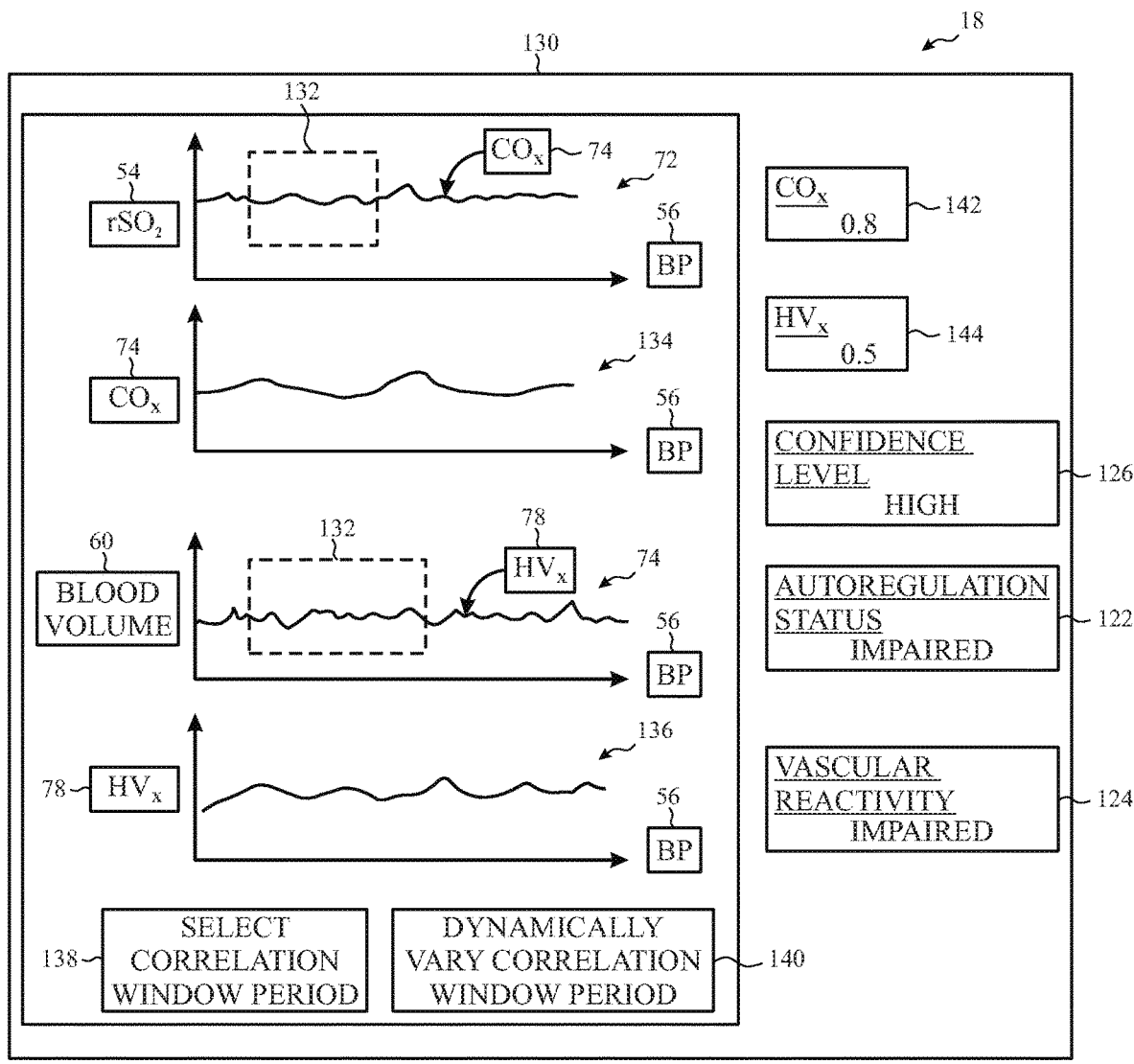
FIG. 6 is a table illustrating example correlations between the cerebral oximetry index, the hemoglobin volume index, an autoregulation status of the patient, a vascular reactivity status of the patient, and a computed confidence level.
FIG. 7 is an embodiment of a display configured to display various information related to monitoring the autoregulation of a patient, including the cerebral oximetry index and the hemoglobin volume index computed over a correlation window.

As discussed in greater detail with respect to FIGS. 5-6, the controller 16 may determine a confidence metric to determine the reliability of the calculated COx or HVx. Indeed, it may be beneficial to determine the reliability of the calculated COx or HVx to accurately monitor the patient's autoregulation. In certain embodiments, the controller 16 may be utilized to determine and display COx on the output device 18 as an indicator of the patient's autoregulation, and may determine HVx in the background as a confidence metric for the COx. Specifically, the controller 16 may assign a high confidence level for the COx if the COx and HVx have the same polarity (e.g., both COx and HVx are positive or both COx and HVx are negative). Likewise, in certain embodiments, the controller 16 may determine and display the HVx on the output device 18 as an indicator of the patient's autoregulation, and may determine COx in the background as a confidence metric for the HVx. In certain embodiments, the controller 16 may determine a confidence metric based on a combination parameter, which may be calculated as the mean or weighted average of the calculated COx and HVx. In certain embodiments, the controller 16 may determine a confidence metric based on a second linear correlation coefficient, which may be calculated by correlating the COx with the HVx. Specifically, the COx values are plotted against the HVx values and the controller 16 may be configured to determine a linear correlation between the values. Further, the controller 16 may be configured to determine a second linear correlation coefficient and utilize the second linear correlation coefficient as the confidence metric.

Figure 8A:
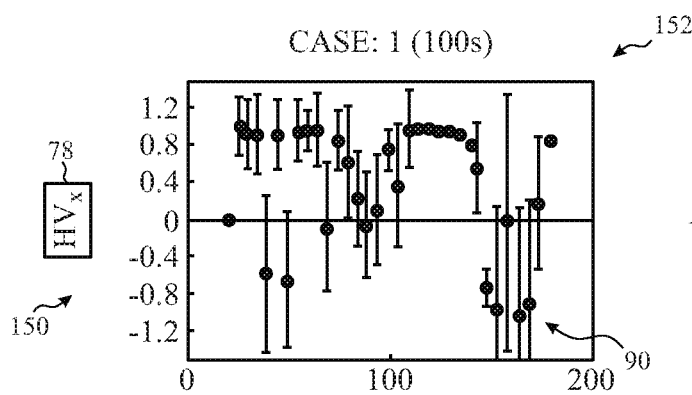
FIGS. 8A-8F are embodiments of graphs depicting the hemoglobin volume index across one or more correlation windows having different periods.
Figure 8B:
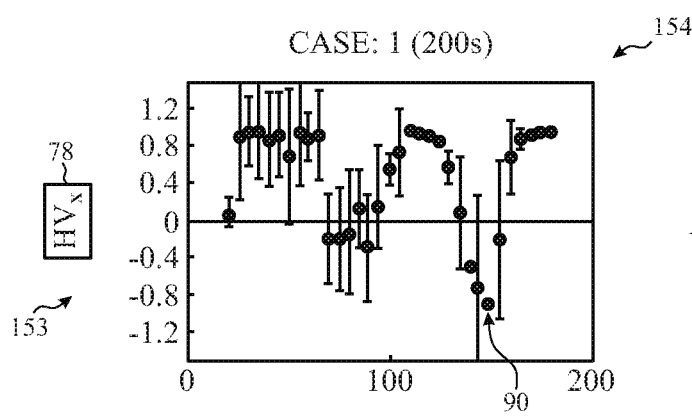
Figure 8C:
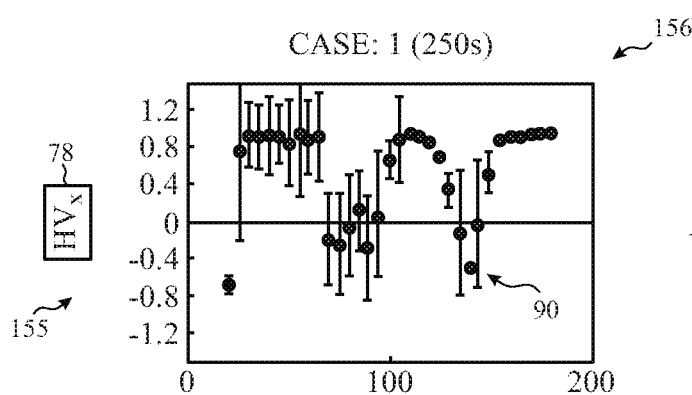
Figure 8D:
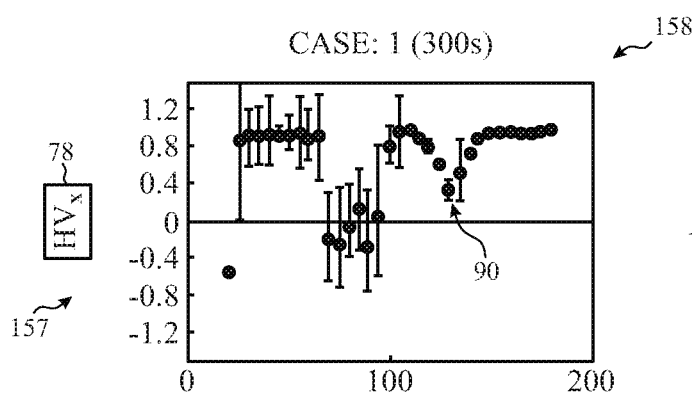
Figure 8E:
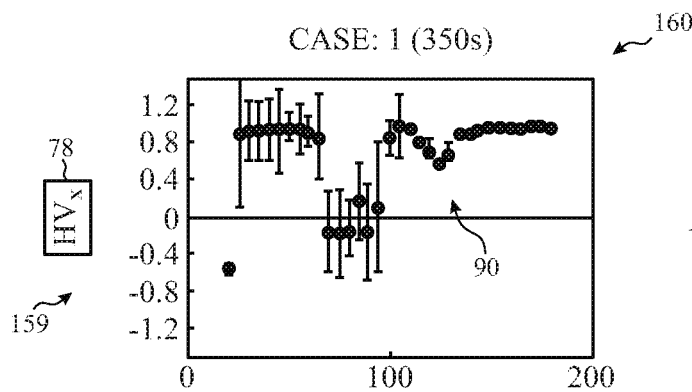
Figure 8F:
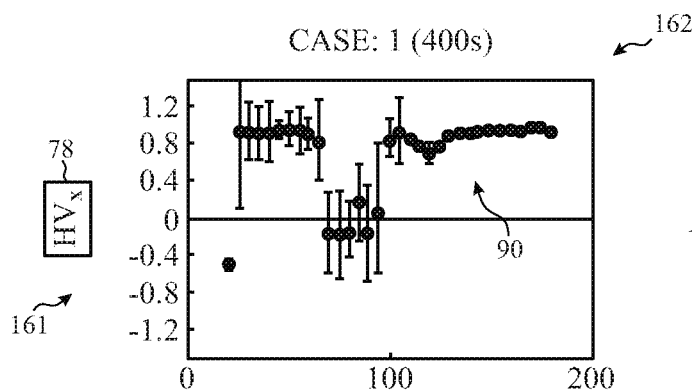
Figure 9:
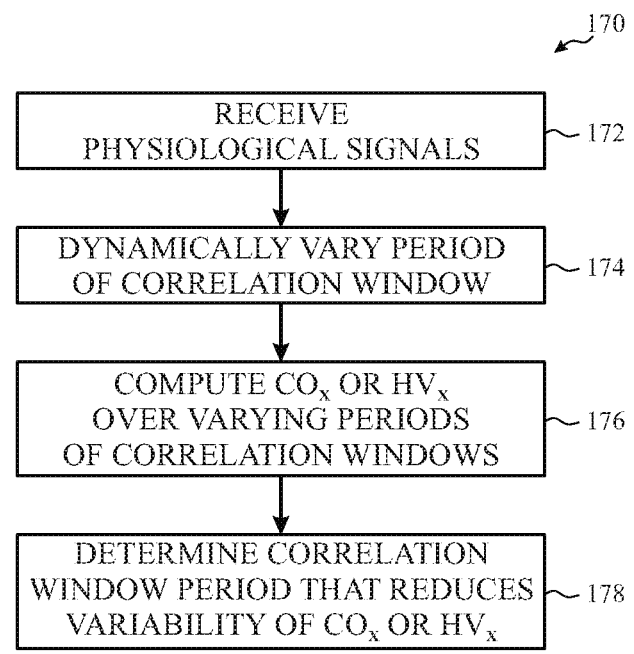
FIG. 9 is a process flow diagram of a method for monitoring autoregulation of a patient based on a correlation window having a period that reduces sources of error, in accordance with an embodiment.

As discussed in greater detail with respect to FIGS. 7-9, the controller 16 may calculate COx or HVx over a correlation window having a particular period. For example, COx may be calculated over a correlation window of 300 seconds for a continuous signal of the oxygen saturation measurements plotted against the blood pressure measurements. The correlation window may have a period of 100 seconds, 150 seconds, 200 seconds, 250 seconds, 300 seconds, 350 seconds, 400 seconds, and so forth. In certain embodiments, the controller 16 may be configured to dynamically vary the period of the correlation window to exclude or ignore portions of the oxygen saturation measurements plotted against the blood pressure measurements with great variability and less stability (e.g., noise). In certain embodiments, such as in situations where the confidence metric indicates that calculated COx or HVx are less reliable, the system may be configured to dynamically vary the period of the correlation window to calculate or recalculate the COx or HVx to reduce the variability and improve the reliability. In some situations, the system may evaluate multiple periods of the correlation window to calculate the COx or HVx from a correlation window having a period that reduces variability resulting from noise. It should be noted that in some situations, the controller 16 may be configured to vary the correlation window to identify one or more stable portions of the COx or HVx, which may be a reliable indication of the patient's autoregulation status. Further, in some embodiments, an operator may manually vary or select the period of the correlation window to prompt the system to calculate or recalculate the COx or HVx.

In the illustrated embodiment, the controller 16 includes a processor 24 and a memory device 26. The controller 16 may also include one or more storage devices. The processor 24 may be used to execute software, such as software for carrying out any of the techniques disclosed herein, such as processing the signals received from the blood pressure sensor 12 or the oxygen saturation sensor 14, determining the COx or HVx values, determining a confidence metric, determining the reliability of the COx or HVx, determining regions of COx or HVx that exhibit stability, varying the period of the correlation window to determine regions of stability, determining an autoregulation status of the patient, carrying out appropriate remedial actions, and so forth. Moreover, the processor 24 may include multiple microprocessors, one or more "general-purpose" microprocessors, one or more special-purpose microprocessors, and/or one or more application specific integrated circuits (ASICS), or some combination thereof. For example, the processor 24 may include one or more reduced instruction set (RISC) processors.

The memory device 26 may include a volatile memory, such as random access memory (RAM), and/or a nonvolatile memory, such as ROM. The memory device 26 may include one or more tangible, non-transitory, machine-readable media collectively storing instructions executable by the processor 24 to perform the methods and control actions described herein. Such machine-readable media can be any available media that can be accessed by the processor 24 or by any general purpose or special purpose computer or other machine with a processor. The memory device 26 may store a variety of information and may be used for various purposes. For example, the memory device 26 may store processor-executable instructions (e.g., firmware or software) for the processor 24 to execute, such as instructions for carrying out any of the techniques disclosed herein, such as processing the signals received from the blood pressure sensor 12 or the oxygen saturation sensor 14, determining the COx or HVx values, determining a confidence metric, determining the reliability of the COx or HVx, determining regions of COx or HVx that exhibit stability, varying the period of the correlation window to determine regions of stability, determining an autoregulation status of the patient, carrying out appropriate remedial actions, and so forth. The storage device(s) (e.g., nonvolatile storage) may include read-only memory (ROM), flash memory, a hard drive, or any other suitable optical, magnetic, or solid-state storage medium, or a combination thereof. The storage device(s) may store data (e.g., the blood pressure value, the oxygen saturation value, the blood volume value, the COx, the HVx, the confidence metric, the confidence level, etc.), instructions (e.g., software or firmware for processing the blood pressure signal, the oxygen saturation signal, and/or the blood volume signal, determining the COx and/or the HVx, determining the confidence metric, dynamically or manually varying the period of the correlation window, determining an autoregulation status of the patient, and/or taking appropriate remedial actions), predetermined thresholds, and any other suitable data.

As shown, the system 10 includes the output device 18. In some embodiments, the controller 16 may be configured to provide signals indicative of the patient's autoregulation status to the output device 18. As discussed in more detail below, the controller 16 may be configured to generate an alarm signal indicative of the patient's autoregulation status and to provide the alarm signal to the output device 18. The output device 18 may include any device configured to receive signals (e.g., the signal indicative of the patient's autoregulation status, the alarm signal, or the like) from the controller 16 and visually and/or audibly output information indicative of the patient's autoregulation status (e.g., the COx value, the HVx value, the COx signal, the HVx signal, an alarm, or the like). For instance, the output device 18 may include a display configured to provide a visual representation of the patient's autoregulation status and/or the alarm signal as determined by the controller 16. Additionally or alternatively, the output device 18 may include an audio device configured to provide sounds in accordance with the alarm signal, the patient's autoregulation status, or both. The output device 18 may be any suitable device for conveying such information, including a computer workstation, a server, a desktop, a notebook, a laptop, a handheld computer, a mobile device, or the like. In some embodiments, the controller 16 and the output device 18 may be part of the same device or supported within one housing (e.g., a computer or monitor).

Figure 2A:
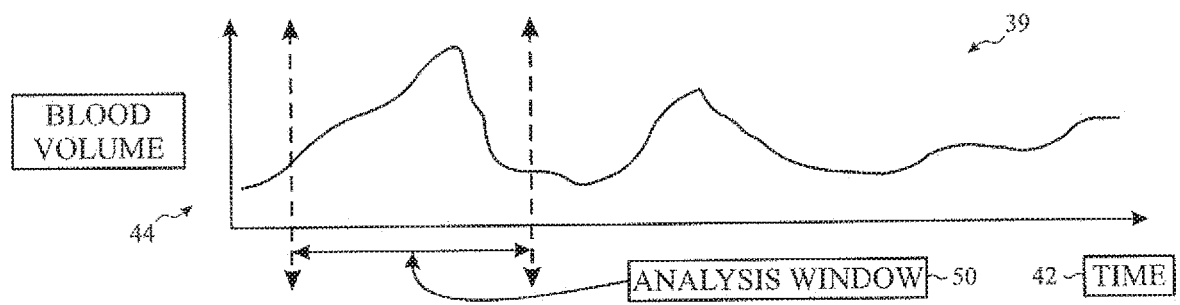
FIG. 2A is an example of a graph illustrating a blood volume signal obtained from the patient over a period of time.
Figure 2B:
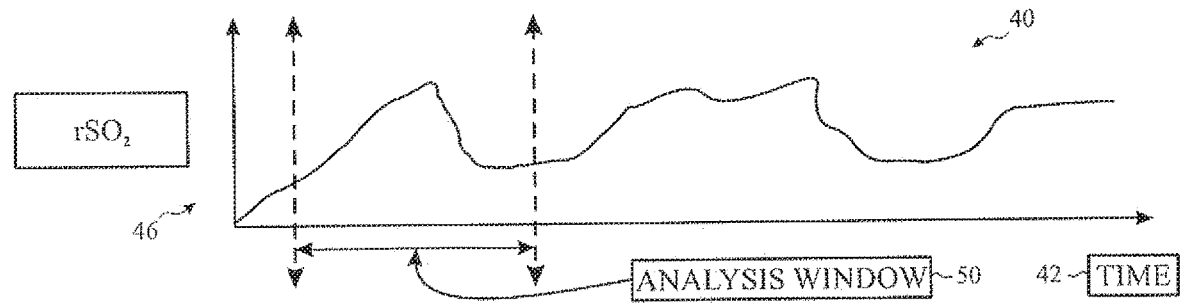
FIG. 2B is an example of a graph illustrating a oxygen saturation signal obtained from the patient over a period of time.
Figure 2C:
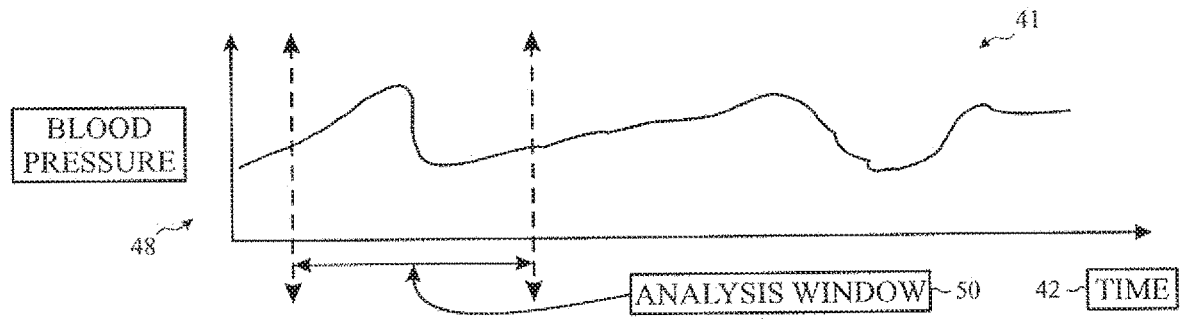
FIG. 2C is an example of a graph illustrating a blood pressure signal obtained from the patient over a period of time.

FIGS. 2A-2C are examples of graphs illustrating physiological values obtained from the patient over a period of time 42 from one or more sensors. Specifically, FIG. 2A is an example of a graph 39 illustrating a blood volume value 44 obtained from the patient over the period of time 42. Further, FIG. 2B is an example a graph 40 illustrating an oxygen saturation value 46 (e.g., regional oxygen saturation value, $rSO_2$, etc.) obtained from the patient over the period of time 42. In addition, FIG. 2C is an example of a graph 41 illustrating a blood pressure value 48 obtained over the period of time 42. As an example, the blood pressure value 48 is described in mmHg units, however, any appropriate unit or measurement may be utilized. It should be noted that the blood volume value 44, the oxygen saturation value 46, and/or the blood pressure value 48 may be obtained from one or both of the blood pressure sensor 12 and the oxygen saturation sensor 14. The period of time 42 over which the physiological values are measured may be different for each signal and/or each sensor, and may be provided to the controller 16 continuously or intermittently over the period of time 42. As noted above, in certain embodiments, other types of physiological values may be measured and provided to the controller 16, such as any physiological signal that may be useful in determining an autoregulation status of a patient (e.g., intracranial pressure, blood flow, cerebral blood flow, etc.).

The controller 16 may be configured to monitor autoregulation of a patient based on one or more of the physiological values received from the patient. Specifically, the controller 16 may determine the COx based in part on a linear correlation between the oxygen saturation signal 46 and the blood pressure signal 48, and utilize the COx as an indicator of the patient's autoregulation. In particular, the controller 16 may be configured to plot oxygen saturation measurements derived from the oxygen saturation signal 46 against blood pressure measurements derived from the blood pressure signal 48 over an overlapping analysis window 50 having a particular length of time. The analysis window 50 may be any portion of the period of time 42 where two physiological values are measured from the same patient at the same time. As described in detail with respect to FIG. 3A, the controller 16 may be configured to plot the oxygen saturation measurements against the blood pressure measurements over the analysis window 50 to determine a linear correlation between measurements obtained at the same time.

Further, in certain embodiments, the controller 16 may determine the HVx based on the linear correlation between the blood volume signal 44 and the blood pressure signal 48, and utilize the HVx as an indicator of the patient's autoregulation status. Accordingly, the controller 16 may be configured to plot blood volume measurements derived from the blood volume signal 44 against blood pressure measurements derived from the blood pressure signal 48 over the overlapping analysis window 50. As described in detail with respect to FIG. 3B, the controller 16 may be configured to plot the blood volume measurements against the blood pressure measurements over the analysis window to determine a linear correlation between the measurements obtained at the same time. It should be noted that the controller 16 may determine both the COx and HVx, so that one may be used as the confidence metric for the other when determining the reliability of the patient's autoregulation. Further, in situations where the controller 16 utilizes the HVx as a confidence metric for the COx or utilizes COx as a confidence metric for the HVx, the analysis window 50 may be the same across the physiological measurements utilized to calculate the COx and HVx.

Figure 3A:
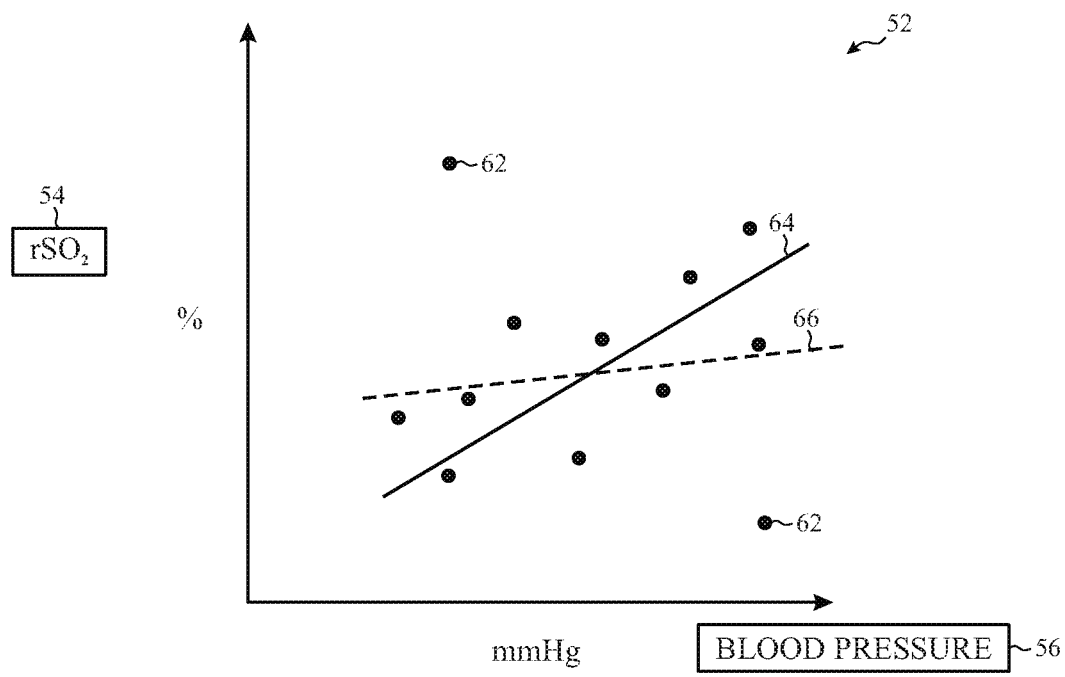
FIG. 3A is an example of a first graph illustrating linear correlations between the oxygen saturation measurements obtained from the oxygen saturation signal of FIG. 2B and the blood pressure measurements obtained from the blood pressure signal of FIG. 2C.
Figure 3B:
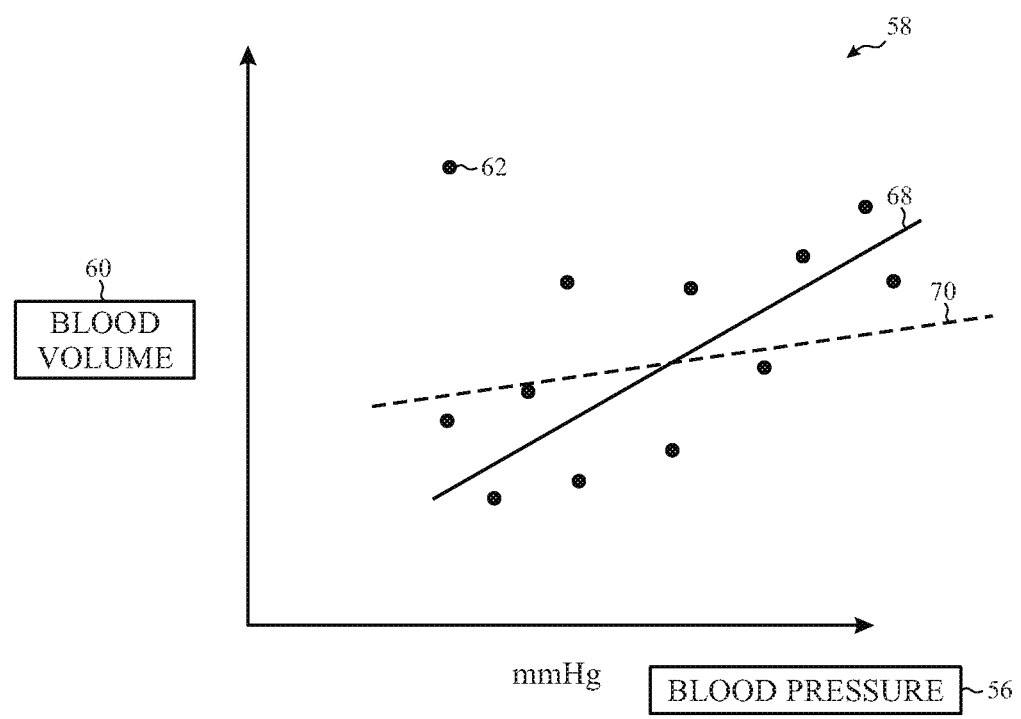
FIG. 3B is an example of a second graph illustrating linear correlations between the blood volume measurements obtained from the blood volume signal of FIG. 2A and the blood pressure measurements obtained from the blood pressure signal of FIG. 2C.

FIG. 3A is an example of a first graph 52 illustrating linear correlations between the oxygen saturation measurements 54 (e.g., regional oxygen saturation measurements) plotted against the blood pressure measurements 56. In addition, FIG. 3B depicts an example of a second graph 58 illustrating linear correlations between the blood volume measurements 60 plotted against the blood pressure measurements 56. As noted above, the oxygen saturation measurements 54, the blood volume measurements 60, and the blood pressure measurements 56 may be derived from the oxygen saturation value 46, the blood volume value 44, and the blood pressure value 48, respectively. Additionally, as noted above, the physiological measurements may be plotted against each other over the analysis window 50.

Specifically, in certain embodiments, the controller 16 may utilize various linear regressions analyses to determine a best fit regression line that fits the physiological measurements. Existing systems may utilize a least squares method (LS) to fit, for example, the oxygen saturation measurements plotted against the blood pressure measurements to determine a regression line associated with the COx. However, the least squares linear regression method may be more susceptible to outliers 62 (e.g., measurements indicative of noise), and the LS fit may not be a reliable indicator of the patient's autoregulation, as further described below. Accordingly, the present embodiments describe utilizing a least median of squares (LMS) regression method to fit the physiological measurements, which may be more robust to outliers 62 and may be a more reliable indicator of the patient's autoregulation, as further described below.

In certain embodiments, the controller 16 may utilize a LMS regression method to determine a LMS regression line 64 indicative of a linear correlation between the oxygen saturation measurements 54 plotted against the blood pressure measurements 56. Indeed, as illustrated within the first graph 52, the LMS regression line 64 may be less susceptible to the outliers 62 than a typical LS regression method that existing systems may use to determine a LS regression line 66. Likewise, as illustrated in the second graph 58, the controller 16 may utilize the LMS regression method to determine a LMS regression line 68 between the blood volume measurements 60 plotted against the blood pressure measurements 56, where the LMS regression line 68 is indicative of HVx. As noted above, the LMS regression line 68 may be less susceptible to outliers 62 than a typical LS regression line 70 that may be used by existing systems. In this manner, the controller 16 may ignore or exclude outliers 62 representative of noise or low quality measurements and utilize the remaining measurements to determine the LMS regression lines 64, 68.

Further, in certain embodiments, the controller 16 may receive signal quality metrics associated with the oxygen saturation signal 46, the blood volume signal 44, and/or the blood pressure signal 48, and may utilize the signal quality metrics to determine and/or exclude portions of the measurements (e.g., outliers 62). The quality metric may be indicative of the accuracy of the signal and may be calculated based on one or more signal quality indicators. Any suitable signal quality indicators may be considered, including a signal measure indicative of a low light level; a signal measure indicative of an arterial pulse shape; a signal measure indicative of the high frequency signal component in the measured value; a signal measure indicative of a consistency of a pulse shape; a signal measure indicative of an arterial pulse amplitude; and a signal measure indicative of a period of an arterial pulse, for example. These various indicators provide an indirect assessment of the presence of known error sources in blood pressure or oxygen saturation values, which include optical interference between the sensor and the tissue location, physical movement of the patient, and/or improper tissue-to-sensor positioning, for example. Accordingly, the controller 16 may be configured to exclude specific portions of the measurements and/or set a predetermined number of outliers 62 to be excluded based on one or more quality metrics related to the received physiological values. Further, the remaining measurements may be utilized to determine the LMS regression lines 64, 68.

In certain embodiments, other types of regression methods may be utilized to determine regression lines that are more robust and less susceptible to outliers 62. For example, a least trimmed squares method (LTS) may be used to exclude one or more specific portions of the measurements and/or a predetermined number of outliers 62. Accordingly, the LTS method may be used to fit the remaining measurements that are a more reliable indicator of the patient's physiological condition, and therefore a more reliable indicator of the patient's autoregulation status. Accordingly, the controller 16 may be configured to apply a least median of squares (LMS) regression method or a least trimmed squares (LTS) regression method to measurements to determine the COx or HVx. Indeed, COx or HVx calculated using the LMS regression or the LTS regression methods may have less variability due to signal noise and may be less susceptible to data outliers, as further described with respect to FIGS. 4A and 4B.

The result of the linear correlation may be the regression lines 64, 66, 68, and 70 between the physiological measurements, and the slope of the regression lines 64, 66, 68, and 70 may be indicative of the patient's autoregulation status. In certain situations, the slope of the regression lines 64, 66, 68, and 70 may also be known as the polarity of the calculated COx or HVx. For example, the slope and/or polarity of the LMS regression line 64 is negative and, thus, the COx value is between −1 and 0, which may indicate proper autoregulation. In such cases, the controller 16 may determine that the patient's cerebral autoregulation is functioning properly and may generate and/or output an appropriate signal indicative of the patient's autoregulation status to the output device 18, for example. However, when the LMS regression line 64 has a positive slope and/or polarity and the COx value is between 0 and 1 or above some predetermined threshold (e.g., 0.1, 0.2, 0.3, 0.4, 0.5, 0.6, 0.7, 0.8 or 0.9, as discussed above), the controller 16 may determine that the patient's autoregulation is impaired and may generate and/or output the appropriate signal indicative of the patient's autoregulation status.

Figure 4A:
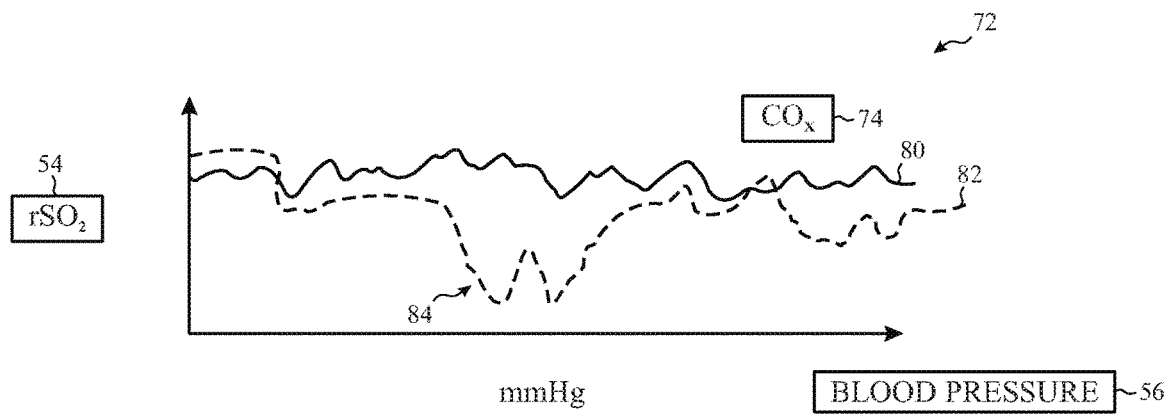
FIG. 4A is an example of a first graph illustrating a cerebral oximetry index obtained from the first graph of FIG. 3A.
Figure 4B:
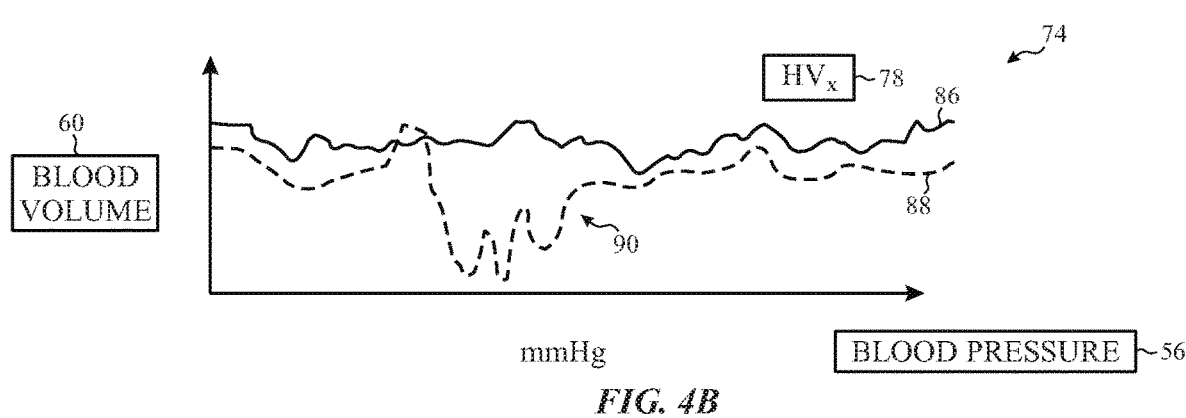
FIG. 4B is an example of a second graph illustrating a hemoglobin volume index obtained from the second graph of FIG. 3B.

FIG. 4A is an example of a first graph 72 illustrating a cerebral oximetry index 74 (COx 74) obtained from the first graph 52 of FIG. 3A. In addition, FIG. 4B is an example of a second graph 74 illustrating a hemoglobin volume index 78 (HVx 78) obtained from the second graph 58 of FIG. 3B. The first graph 72 illustrates the COx measure 74 as a continuous signal derived from the oxygen saturation measurements 54 plotted against the blood pressure measurements 56. Specifically, the first graph 72 illustrates a LMS COx measure 80 that may be calculated as a result of applying the LMS regression method to the oxygen saturation measurements 54 and the blood pressure measurements 56. As noted above, linear correlations calculated utilizing the LMS regression method may have less variability due to signal noise and may be less susceptible to outliers 62. Indeed, as illustrated in the first graph 72, the LMS COx measure 80 depicts less variability than a LS COx measure 82 that is derived from a LS regressions method between the oxygen saturation measurements 54 and the blood pressure measurements 56. For example, the LS COx measure 82 may exhibit regions or portions of high variability 84 that may be indicative of unreliable portions of the COx that may be a result of signal noise. Similarly, the second graph 74 illustrates the HVx measure 78 as a continuous signal derived from the blood volume measurements 60 plotted against the blood pressure measurements 56. Specifically, the second graph 74 illustrates a LMS HVx measure 86 that may have less variability due to signal noise and may be less susceptible to outliers 62 than a LS HVx measure 88. As noted above, utilizing the LMS regression method to calculate the LMS HVx measure 86 may help reduce the effect of outliers 62 (e.g., data associated with signal noise), which may otherwise cause regions of high variability 90 within the calculated LS HVx measure 88.

FIG. 5 is a process flow diagram of a method 100 of monitoring autoregulation based on a confidence metric, in accordance with an embodiment. Some or all of the steps of the method 100 may be implemented by the controller 16 (e.g., the processor 24 of the controller 16) of FIG. 1, for example, to determine whether the patient's autoregulation is impaired and/or to take an appropriate remedial action. In step 102, the controller 16 may receive one or more physiological values, such as, for example, the blood pressure signal 48 (e.g., arterial blood pressure signal), the oxygen saturation signal 46, and/or the blood volume signal 44 from the blood pressure sensor 12 and/or the oxygen saturation sensor 14.

In step 104, the controller 16 may determine the COx 74 based in part on the linear correlation between blood pressure measurements 56 and the oxygen saturation measurements 54. As noted above, the controller 16 may determine the linear correlation between blood pressure measurements 56 and the oxygen saturation measurements 54 with a least median of squares (LMS) regression. Specifically, the controller 16 may use the LMS regression to determine the LMS regression line 64 that ignores or excludes data outliers 62 representative of noise. Further, as noted above, the controller 16 may calculate the COx based on the slope of the LMS regression line 64. Likewise, in step 106, the controller 16 may determine the HVx based on the linear correlation between blood volume measurements 60 and the blood pressure measurements 56. While in certain embodiments, COx is calculated as an indicator of the patient's autoregulation, in some embodiments, HVx may be calculated as an indicator of the same. Further still, in certain embodiments, both COx and HVx may be calculated, and one or more of the calculated COx and HVx may be utilized to determine the reliability of the calculated COx or HVx.

In step 108, the controller 16 may be configured to determine a confidence metric in order to determine the reliability of the calculated COx or HVx. For example, in certain embodiments, the controller 16 may determine and display COx on the output device 18 as an indicator of the patient's autoregulation, and may determine HVx in the background as a confidence metric for the COx. Specifically, the controller 16 may compare the polarity (e.g., slope) of the regression line associated with COx with the polarity (e.g., slope) of the regression line associated with HVx to determine the level of confidence to assign COx, as further described with respect to FIG. 6. For example, if both COx and HVx have a positive polarity (e.g., greater than 0) or if both COx and HVx have a negative polarity (e.g., less than 0), the controller 16 may assign a high level of confidence to COx, and may display COx on the output device 18 as a reliable indicator of the patient's autoregulation. As a further example, when the polarity of COx is negative, the controller 16 may determine that the patient's cerebral autoregulation is intact and functioning properly. Accordingly, if the polarity of HVx is also negative, the controller 16 may determine with a high level of confidence that the patient's cerebral autoregulation is intact. Likewise, in certain embodiments, the controller 16 may determine and display HVx on the output device 18 as an indicator of the patient's autoregulation, and may determine COx in the background as a confidence metric for the HVx.

In certain embodiments of step 108, the controller 16 may determine a confidence metric based on a combination parameter, which may be calculated as the mean or weighted average of the COx and HVx. Further, the combination parameter may be compared against a pre-determined threshold or value to determine the level of confidence to assign to the COx and/or the HVx. In certain embodiments of step 108, the controller 16 may be configured to determine the confidence metric based on a linear correlation confidence coefficient, which may be calculated by correlating the COx with the HVx. For example, the controller 16 may determine a linear correlation between COx values and HVx values using one or more of the methods described with respect to FIGS. 2-3. Specifically, the controller 16 may be configured to determine a linear correlation confidence coefficient, which may be between −1 and +1, inclusive, where −1 represents total negative correlation, +1 represents total positive correlation, and 0 represents the absence of correlation between the HVx and COx values. Thus, a positive linear correlation confidence coefficient may suggest a high confidence and high reliability in the calculated values, while a negative linear correlation confidence coefficient may suggest a low confidence and reliability.

In step 110, the controller 16 may be configured to evaluate a confidence level for the COx or HVx. In certain embodiments, the confidence level may be indicated as "high" or "low," while in other embodiments, the confidence level may be associated with a percent confidence, as further described below. If the confidence level is high, the determined COx and/or HVx measures and the associated autoregulation status of the patient is output to the output device 18 in step 112. In some embodiments, information related to the autoregulation of the patient is displayed on the output device 18, as further described with respect to FIG. 7. Further, the controller 16 may continue to monitor the patient's autoregulation status by continuing to receive physiological values (step 102). If the confidence metric is not high (e.g., a low or unacceptable confidence level in the COx and/or the HVx), the controller 16 may take appropriate remedial action in step 114. For example, the controller 16 may discard the COx and/or may not provide the COx to the output device 18. In some situations, such as when the currently computed COx value is an average or a weighted average of previously computed COx values, the controller 16 may not use the currently computed COx value in the average or weighted average if the confidence metric is unacceptable. Further, in some situations, if the confidence metric is low or unacceptable, the currently computed COx value may be assigned a lower weighting within the weighted average. In some cases, the controller 16 may cause the output device 18 to display a blank display screen or provide an appropriate visual or audible indication that the COx and/or HVx is unavailable. In certain embodiments, the controller 16 may hold or maintain the COx and/or HVx value immediately preceding the segment determined to be unreliable, and thus may cause the output device 18 to show the most recent reliable COx and/or HVx value for a set period of time (e.g., 5, 10, 20, 30, 40, 50, 60 seconds or more) or until the confidence metric is acceptable. In some embodiments, the controller 16 may be configured to average the unreliable COx and/or HVx value(s) with the most recent reliable COx and/or HVx value(s), and may cause the output device 18 to provide an appropriate visual or audible indication of this average COx and/or HVx value.

FIG. 6 is a table 120 illustrating example correlations between the COx 74, the HVx 78, an autoregulation status 122 of the patient, a vascular reactivity 124 of the patient, and the computed confidence level 126. As noted above with respect to FIG. 5, in some situations, the controller 16 may determine and display COx on the output device 18 as an indicator of the patient's autoregulation, and may determine HVx in the background as a confidence metric for the COx. Specifically, the controller 16 may compare the polarity (e.g., slope) for COx with the polarity for HVx to determine the confidence level 126 to assign COx. For example, as illustrated in table 120, if both COx and HVx have a negative polarity (e.g., less than 0), the controller 16 may assign a high confidence level 126 that the calculated COx correlates to an intact autoregulation status 122. Likewise, if both COx and HVx have a positive polarity (e.g., greater than 0), the controller 16 may assign a high confidence level 126 that the calculated COx correlates to an impaired autoregulation status 122. In addition, if COx has a positive polarity and HVx has a negative polarity (e.g., opposite polarities), the controller 16 may assign a low confidence level 126 that the calculated COx is impaired. Likewise, if COx has a negative polarity and HVx has a positive polarity, the controller 16 may assign a low confidence level 126 that the calculated COx is intact. In this manner, the controller 16 may determine the reliability of the calculated COx to determine an accurate autoregulation status 122 for monitoring and diagnostic purposes. Furthermore, it should be noted that the controller 16 may determine and display HVx on the output device 18 as an indicator of the patient's autoregulation, and may determine COx in the background as a confidence metric for the HVx. In these embodiments, the controller 16 may utilize the vascular reactivity 124 of the patient as an indication of the autoregulation status 122 of the patient. Further, the confidence level 126 determined may be provided in a variety of different descriptive ways. For example, in certain embodiments, the confidence level 126 may be presented as a high percent confidence (e.g., 75, 80, 95, or more percent) or a low percent confidence (e.g., 30, 35, 45 or less percent).

In certain embodiments, the polarity of the COx and/or HVx may be determined in relation to a non-zero threshold. For example, in certain embodiments, the controller 16 may set the threshold to 0.2, so that a positive polarity is any value greater than 0.2 and a negative correlation is any value less than 0.2. It should be noted that any number may be designated as the non-zero threshold. In addition, in certain embodiments, the table 120 may be adapted for correlations between the combination parameter (e.g., mean or weighted average of the COx and HVx) and the autoregulation status 122 and vascular reactivity 124 of the patient. Likewise, in certain embodiments, the table 120 may be adapted for correlations between the linear correlation confidence coefficient (e.g., mean or weighted average of the COx and HVx) and the autoregulation status 122 and vascular reactivity 124 of the patient.

FIG. 7 is an embodiment of a display 130 of the output device 18 that is configured to display various information related to monitoring the autoregulation of a patient. As illustrated in FIG. 7, the display 130 may include a correlation window 132 that incrementally scans the first graph 72 and/or the second graph 74 to determine a continuous COx 74 and/or a continuous HVx 78, as illustrated in the third graph 134 and fourth graph 136, respectively. The resulting continuous COx 74 and/or HVx 78 may also be provided on the display 130, which may be updated continuously or at predetermined intervals. In particular, the controller 16 may initially set the correlation window 132 to a predetermined period, such as at approximately 300 seconds. In certain embodiments, such as in situations where the controller 16 evaluates a low confidence level 126 of the calculated COx or HVx, the controller 16 may be configured to dynamically vary the period of the correlation window 132 to compute or recompute the COx 74 and/or HVx 78. For example, the controller 16 may vary the correlation window 132 to have a period of 100 seconds, 150 seconds, 200 seconds, 250 seconds, 350 seconds, 400 seconds, and so forth, when incrementally scanning and calculating the continuous COx 74 and HVx 78 measures. It should be noted that varying the correlation window 132 in this manner may allow the controller 16 to find the correlation window 132 with the particular period that reduces the variability in the calculated COx or HVx caused by signal noise.

In certain embodiments, an operator may input or select, such as through a first user input 138 disposed on the display 130, a desired correlation window period 138, and the controller 16 may calculate the COx 74 and/or HVx 78 by incrementally scanning the first and second graphs 72, 74 based on the user input. Further, in certain embodiments, the operator may instruct the controller 16, such as through a second user input 140 disposed on the display 130, to dynamically smooth or vary the correlation window period 140 in order to reduce the influence of data caused by noise or low quality measurements on the calculated COx 74 and/or HVx 78. In particular, varying the period of the correlation window 132 may help to ignore or exclude data that causes high variability within the COx 74 and/or HVx 78, as further described with respect to FIGS. 8A-8F.

As shown, the display 130 may also be configured to provide a COx value 142 and/or an HVx value 144, which may be updated continuously or at predetermined intervals based on the continuous COx 74 and/or HVx 78 measures. In some embodiments, the display 130 may provide an indication of the confidence level 126 related to whether the COx and/or HVx values 142, 144 and COx and/or HVx values 74, 78 are reliable, which may be determined based on a confidence metric, as discussed above. For example, in the illustrated embodiment, the display 130 indicates that the confidence level 126 is high (e.g., 75, 95, 99 percent confident, or the like), and that the autoregulation status 122 and vascular reactivity status 124 of the patient are impaired. As noted above, the COx value 142 of 0.8 and an HVx value 144 of 0.5 may indicate an impaired autoregulation status 122 and an impaired vascular reactivity status 124. Further, a comparison of the COx value 142 of 0.8 and an HVx value 144 of 0.5 may indicate a positive polarity for both, resulting in the high confidence level 126, and thus the display 130 may be configured to provide a reliable indication of the patient's autoregulation status.

FIGS. 8A-8F illustrates embodiments of graphs depicting the HVx 78 as it varies between correlation windows 132 having different periods (e.g., window lengths). Specifically, as noted above, the correlation window 132 may have a period of 100 seconds, 150 seconds, 200 seconds, 250 seconds, 300 seconds, 350 seconds, 400 seconds, and so forth. In certain embodiments, the controller 16 may compute the COx 74 and/or HVx 78 across a correlation window 132 having a period of 300 seconds. In some situations, the controller 16 may dynamically vary the correlation window 132 to compute several different COx 74 and/or HVx 78 measures. Specifically, varying the correlation window 132 may smooth or exclude one or more portions of the data to reduce the variability in the calculated COx or HVx caused by signal noise. In certain embodiments, the controller 16 may vary the correlation window 132 to identify a stable region within the COx or HVx that may be a reliable indication of the patient's autoregulation status.

With the foregoing in mind, FIG. 8A illustrates a graph 150 depicting the HVx 78 calculated over a first correlation window 152 having a period of 100 seconds, FIG. 8B illustrates a graph 153 depicting the HVx 78 calculated over a second correlation window 154 having a period of 200 seconds, FIG. 8C illustrates a graph 155 depicting the HVx 78 calculated over a third correlation window 156 having a period of 250 seconds, FIG. 8D illustrates a graph 157 depicting the HVx 78 calculated over a fourth correlation window 158 having a period of 300 seconds, FIG. 8E illustrates a graph 159 depicting the HVx 78 calculated over a fifth correlation window 160 having a period of 350 seconds, and FIG. 8F illustrates a graph 161 depicting the HVx 78 calculated over a sixth correlation window 162 having a period of 400 seconds. In particular, as illustrated with FIGS. 8A-8F, the variability 90 decreases as the period of the correlation windows 132 increases from 100 seconds to 400 seconds. In this manner, in certain embodiments, the controller 16 may be configured to calculate the correlation window 132 for one or more periods, and may choose the most appropriate correlation window 132 based on the variability of the HVx within each correlation window 132. For example, as illustrated in the series of graphs 150, 153, 155, 157, 159, and 161, the controller 16 may be configured to evaluate the patient's autoregulation based on the HVx 78 determined from the sixth correlation window 162, since the period of the sixth correlation window 162 reduces the variability of the HVx 78 caused by signal noise.

In certain embodiments, the controller 16 may determine the appropriate period for the correlation window 132 based on one or more quality metrics received from the physiological values. For example, as noted above, the controller 16 may receive signal quality metrics associated with the oxygen saturation signal 46, the blood volume signal 44, and/or the blood pressure signal 48, and may utilize the signal quality metrics to determine and/or exclude portions of the data associated with signal noise. Accordingly, in certain embodiments, the controller 16 may determine the period of the correlation window 16 based on one or more signal quality metrics of the physiological values, such as the shape of the signal.

FIG. 9 is a process flow diagram of a method 170 for monitoring autoregulation of a patient based on dynamically or manually varying the period of the correlation window 132. Some or all of the steps of the method 170 may be implemented by the controller 16 (e.g., the processor 24 of the controller 16) of FIG. 1, for example, to determine the autoregulation status of the patient based on a reliable COx 74 and/or HVx 78. In step 172, the controller 16 may receive one or more physiological values, such as, for example, the blood pressure signal 48 (e.g., arterial blood pressure signal), the oxygen saturation signal 46, and/or the blood volume signal 44 from the blood pressure sensor 12 and/or the oxygen saturation sensor 14. In step 174, the controller 16 may dynamically vary the period of the correlation window 132 between one or more different periods (e.g., 100 seconds, 150 seconds, 200 seconds, 250 seconds, 350 seconds, 400 seconds, and so forth). In step 176, the controller 16 may compute the COx 74 and/or the HVx 78 for each period of the correlation window 132. For example, the controller 16 may dynamically vary the period of the correlation window 132 to calculate one or more HVx 78 or COx 74 measures, and may select an appropriate index based on the detected variability or stability. Further, in certain embodiments, an operator may select the period of the correlation window 132 based on visually inspecting one or more parameters related to autoregulation displayed on the display 130. Accordingly, in step 178, the controller 16 may determine one or more periods of the correlation window 132 that reduces variability in the calculated COx 74 and/or HVx 78 that may be caused by noise or low quality measurements. The controller 16 may be configured to determine the autoregulation status of a patient based on the COx 74 and/or HVx 78 calculated from a selected window.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims. Further, it should be understood that certain elements of the disclosed embodiments may be combined or exchanged with one another.

What is claimed is:

1. A method for monitoring autoregulation of a patient, the method comprising:
    receiving, by one or more processors, a blood pressure signal indicative of a blood pressure of the patient, a regional oxygen saturation signal indicative of a blood oxygen saturation of the patient, and a blood volume signal indicative of a blood volume of the patient;
    determining, by the one or more processors, a first linear correlation between the blood pressure signal and the regional oxygen saturation signal;
    determining, by the one or more processors, a second linear correlation between the blood pressure signal and the blood volume signal;
    determining, by the one or more processors, a linear correlation confidence coefficient, wherein determining the linear correlation confidence coefficient comprises correlating the first linear correlation and the second linear correlation;
    determining, by the one or more processors, a confidence level based on the linear correlation confidence coefficient, wherein the confidence level comprises a percent confidence indicative of a reliability of the determined first linear correlation, the reliability being based on signal noise in the blood pressure signal or the regional oxygen saturation signal;
    determining, by the one or more processors, a value indicative of autoregulation status of the patient based on the first linear correlation and the confidence level;
    determining, by the one or more processors, the confidence level is high by at least comparing the confidence level to a predetermined threshold or value; and
    in response to determining the confidence level is high, at least one of:
        presenting, via a display, information indicative of the autoregulation status of the patient; or
        outputting, via an audio device, information indicative of the autoregulation status of the patient,
        wherein the information indicative of the autoregulation status of the patient is based on the value indicative of the autoregulation status of the patient.

2. The method of claim 1, wherein determining the confidence level further comprises comparing, by the one or more processors, the first linear correlation to the second linear correlation.

3. The method of claim 1, wherein determining the confidence level further comprises comparing, by the one or more processors, a first polarity of the first linear correlation to a second polarity of the second linear correlation.

4. The method of claim 3, further comprising, when either both the first and second polarities are positive or both the first and second polarities are negative, providing a cerebral oximetry index value to at least one of the display or the audio device.

5. The method of claim 1, wherein determining the first and second linear correlations comprises determining the first and second linear correlations based on a least median of squares regression method or a least trimmed squares regression method.

6. The method of claim 5, wherein the least median of squares regression method or the least trimmed squares regression method exclude portions of the blood pressure signal, the regional oxygen saturation signal, or the blood volume signal associated with signal noise.

7. The method of claim 1, wherein determining the first linear correlation comprises determining the first linear correlation between the blood pressure signal and the oxygen saturation signal over a correlation window having a first period.

8. The method of claim 7, further comprising varying the first period of the correlation window to reduce variability associated with signal noise within the first linear correlation.

9. The method of claim 1, wherein determining the confidence level is high further comprises determining, by the one or more processors, the confidence level is high by at least comparing the linear correlation confidence coefficient to a second predetermined threshold.

10. A monitor for monitoring autoregulation of a patient, the monitor comprising:
   at least one of a display or an audio device; and
   one or more processors configured to:
      receive a blood pressure signal indicative of a blood pressure of the patient, a regional oxygen saturation signal indicative of a blood oxygen saturation of the patient, and a blood volume signal indicative of a blood volume of the patient;
      determine a first linear correlation between the blood pressure signal and the regional oxygen saturation signal;
      determine a second linear correlation between the blood pressure signal and the blood volume signal;
      determine a linear correlation confidence coefficient by at least correlating the first linear correlation and the second linear correlation;
      determine a confidence level based on the linear correlation confidence coefficient, wherein the confidence level comprises a percent confidence indicative of a reliability of the determined first linear correlation, the reliability being based on signal noise in the blood pressure signal or the regional oxygen saturation signal;
      determine a value indicative of autoregulation status of the patient based on the first linear correlation and the confidence level;
      determine the confidence level is high by at least comparing the confidence level to a predetermined threshold or value; and
      in response to determining the confidence level is high, at least one of:
         present, via the display, information indicative of the autoregulation status of the patient; or
         output, via the audio device, information indicative of the autoregulation status of the patient,
         wherein the information indicative of the autoregulation status of the patient is based on the value indicative of the autoregulation status of the patient.

11. The monitor of claim 10, wherein the one or more processors are configured to determine the first and second linear correlations utilizing a least median of squares regression method or a least trimmed squares regression method.

12. The monitor of claim 10, wherein the one or more processors are further configured to determine the confidence level by at least comparing a first polarity of the first linear correlation to a second polarity of the second linear correlation.

13. The monitor of claim 12, wherein the one or more processors are configured to, when either both the first and second polarities are positive or both the first and second polarities are negative, provide a cerebral oximetry index value to at least one of the display or the audio device.

14. The monitor of claim 10, wherein the one or more processors are configured to determine the first linear correlation between the blood pressure signal and the regional oxygen saturation signal over a correlation window comprising a first period.

15. The monitor of claim 14, wherein the one or more processors are configured to vary the first period of the correlation window to reduce variability associated with signal noise within the first linear correlation.

16. A system for monitoring autoregulation of a patient, the system comprising:
   a regional oxygen saturation sensor configured to obtain a regional oxygen saturation signal indicative of a blood oxygen saturation of the patient; and
   a monitor comprising:
      at least one of a display or an audio device; and
      one or more processors configured to:
         receive a blood pressure signal indicative of a blood pressure of the patient, the regional oxygen saturation signal, and a blood volume signal indicative of a blood volume of the patient;
         determine a first linear correlation between the blood pressure signal and the regional oxygen saturation signal;
         determine a second linear correlation between the blood pressure signal and the blood volume signal;
         determine a linear correlation confidence coefficient by at least correlating the first linear correlation and the second linear correlation;
         determine a confidence level based on the linear correlation confidence coefficient, wherein the confidence level comprises a percent confidence indicative of a reliability of the determined first linear correlation, the reliability being based on signal noise in the blood pressure signal or the regional oxygen saturation signal;
         determine a value indicative of autoregulation status of the patient based on the first linear correlation and the confidence level;
         determine the confidence level is high by at least comparing the confidence level to a predetermined threshold or value; and
         in response to determining the confidence level is high, at least one of:
            present, via the display, information indicative of the autoregulation status of the patient; or
            output, via the audio device, information indicative of the autoregulation status of the patient,
            wherein the information indicative of the autoregulation status of the patient is based on the value indicative of the autoregulation status of the patient.

17. The system of claim 16, wherein the regional oxygen saturation sensor is configured to obtain the regional oxygen saturation signal and at least one of the blood volume signal or the blood pressure signal.

18. The system of claim 16, wherein the one or more processors are configured to cause display of a cerebral oximetry index value indicative of the patient's autoregulation status, a hemoglobin volume index, the confidence level associated with the cerebral oximetry index value or the hemoglobin volume index, an indication of the patient's autoregulation status, or any combination thereof.

19. The system of claim 16, wherein the one or more processors are configured to:
- display, via the display, a correlation window comprising a first period; and
- determine the first linear correlation between the blood pressure signal and the regional oxygen saturation signal over the correlation window.

\* \* \* \* \*